(12) United States Patent
Laurie et al.

(10) Patent No.: US 7,932,227 B1
(45) Date of Patent: Apr. 26, 2011

(54) LACRITIN-SYNDECAN FUSION PROTEINS

(75) Inventors: Gordon W. Laurie, Charlottesville, VA (US); Peisong Ma, Charlottesville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 303 days.

(21) Appl. No.: 12/212,517

(22) Filed: Sep. 17, 2008

Related U.S. Application Data

(60) Provisional application No. 60/994,090, filed on Sep. 17, 2007.

(51) Int. Cl.
    *A61K 38/16* (2006.01)
    *A61K 38/17* (2006.01)
    *C07K 14/435* (2006.01)
(52) U.S. Cl. .............................. 514/12; 514/2; 530/350
(58) Field of Classification Search .................. None
    See application file for complete search history.

(56) References Cited

U.S. PATENT DOCUMENTS

| | | | |
|---|---|---|---|
| 7,320,870 | B2 | 1/2008 | Laurie |
| 7,459,440 | B2 | 12/2008 | Laurie |
| 2002/0102604 | A1 | 8/2002 | Milne Edwards |
| 2002/0164669 | A1 | 11/2002 | Ruben |
| 2007/0167371 | A1 | 7/2007 | Laurie |
| 2007/0167372 | A1 | 7/2007 | Laurie |
| 2007/0207522 | A1 | 9/2007 | Laurie |

FOREIGN PATENT DOCUMENTS

| | | |
|---|---|---|
| WO | 9827205 | 6/1998 |
| WO | 9835299 | 8/1998 |
| WO | 02065943 | 8/2002 |
| WO | 2004037167 | 6/2004 |
| WO | 2005119899 | 12/2005 |

OTHER PUBLICATIONS

Wells, J.A. (1990). Additivity of mutational effects in proteins. Biochemistry. 29(37):8509-8517.*

Ngo et al. (1994). Computational complexity, protein structure prediction, and the Levinthal paradox. In Merz and Le Grand (Eds.) The Protein Folding Problem and Tertiary Structure Prediction. Birkhauser:Boston, pp. 491-495.*

C. Hirst, et al., "High Levels of CUG-initiated FGF-2 expression cause chromatin compaction, decreased cardiomyocyte mitosis, and cell death", Molecular and Cellular Biochemistry 246: 111-116, 2003.

M. Beier, et al., "Transforming growth factor beta mediates apoptosis in the ganglion cell layer during all programmed cell death periods of the developing murine retina", Neuroscience Research 56 (2006), 193-203.

Joo-Young IM, et al., "COX-2 Regulates the insulin-like growth Factor I-induced Potentation of $Zn^{2+}$—toxicity in Primary Cortical Culture", Molecular Pharmacology, 66:368-376, 2004.

Zaodung Ling, et al., "Progressive dopamine neuron loss following supra-nigral lipopolysaccharide (LPS) infusion into rats exposed to LPS prenatally", Experimental Neurology 199 (2006), 499-512.

Erina Kuranaga, et al., "Fas/Fas Ligand System in Prolactin-Induced Apoptosis in Rat Corpus Luteum: Possible Role of Luteal Immune Cells", Biochemical and Biophysical Research Communications 260, 167-173 (1999).

Emanuela Matteucci, et al., "Hepatocyte growth factor induces apoptosis through the extrinsic pathway in hepatoma cells: favouring role of hypoxia-inducible factor-1 deficiency", Oncogene (2003) 22, 4062-4073.

Doug Lobner, et al., "Mechanisms of bFGF and NT-4 potentiation of necrotic neuronal death", Brain Research 954, (2002) 42-50.

Victor T. Solovyan, et al., "Proteolytic Activation of Latent TGF-β Precedes Caspase-3 Activation and Enhances Apoptotic Death of Lung Epithelial Cells", Journal of Cellular Physiology 207:445-453 (2006).

Vincenzo C. Russo, et al., "Fibroblast Growth Factor-2 Over-Rides Insulin-like Growth Factor-I Induced Proliferation and Cell Survival in Human Neuroblastoma Cells", Journal of Cellular Physiology 199:371-380 (2004).

Heidi M. Sowter, et al., "Predominant Role of Hypoxia-Inducible Transcription Factor (Hif)-1α versus Hif-2α in Regulation of the Transcriptional Response to Hypoxia[1]", Cancer Research 63, 6130-6134, Oct. 1, 2003.

Sandhya Sanghi, et al., "cDNA and Genomic Cloning of Lacritin, a Novel Secretion Enhancing Factor from the Human Lacrimal Gland", Journal of Molecular Biology, Jun. 2001, vol. 310, No. 29, pp. 127-139.

A.J. Lumdsden, et al., "Paired Oligonucleotide Screening for BM180 in a Human Lacrimal Gland cDNA Library:Clone HL-2," American Society for Cell Biology Annual Meeting (1998).

Sandhya Sanghi, et al., "cDNA Cloning and Expression of 'lacritin', a Novel Secreted Glycoprotein of the Lacrimal Gland", American Society for Cell Biology Annual Meeting (1999).

Sandhya Sanghi, et al., "Quantitation of Rat Lacrimal Secretion: a Novel Sandwich ELISA with High Sensitivity," Experimental Eye Research, Academic Press (2000).

Rudinger, J., et al., "Characteristics of the amino acids as components of a peptide hormone sequence", Peptide Hormones, University Park Press (Baltimore), Jun. 14, 1976.

Bork, Peer; "Powers and Pitfalls in Sequence Analysis" The 70% Hurdle, Genome Research, 2000, 10: 398-400, Cold Spring Harbor Laboratory Press.

Skolnick, et. al., "From Genes to Protein Structure and Function: Novel Applications of Computational Approaches in the Genomic Era", TIBTECH, Jan. 2000, vol. 18: 34-39.

Doerks, et. al., "Protein Annotation: Detective Work for Function Prediction", Trends in Genetics, Jun. 1998, vol. 14, No. 6: 248-250.

Smith, et. al., "The Challenges of Genome Sequence Annotation or 'The Devil is in the Details'", Nature Biotechnology, Nov. 1997, vol. 15: 1222-1223.

(Continued)

*Primary Examiner* — Christine J Saoud
*Assistant Examiner* — Jon M Lockard
(74) *Attorney, Agent, or Firm* — Rodney L. Sparks

(57) ABSTRACT

The present invention relates to methods and compositions useful for the regulation of lacritin, syndecan, and lacritin-syndecan interactions and the signaling pathway downstream of lacritin-syndecan interactions. The invention also relates to regulating lacritin-syndecan interaction to regulate ocular cell survival in response to an insult or injury, in protecting against ocular inflammation, and in promoting ocular wound repair.

3 Claims, 18 Drawing Sheets
(1 of 18 Drawing Sheet(s) Filed in Color)

OTHER PUBLICATIONS

Boraschi, et. al., "Interleukin-1 and Interleukin-1 Fragments as Vaccine Adjuvants", 1999, Methods, 19:108-113.

Prabhakaran, et. al., "Sequencing and Model Structure of a Naja naja atra Protein Fragment", Journal of Peptide Research, 2000, 56: 12-23.

Fritz, Gerhard, "Molecules in focus—Human APE/Ref-1 Protein", Int. Journal of Biochemistry, 2000, 32: 925-929.

Ma, et. al', "Heparanase Deglycanation of Syndecan-1 is Required for Binding of the Epithelial-Restricted Prosecretory Mitogen Lacritin", Journal of Cell Biology, Sep. 25, 2006, vol. 174, No. 7, 1097-1106.

Wang et al., "Restricted Epithelial Proliferation by Lacritin via PKCα-dependent NFAT and mTOR Pathways", Journal of Cell Biology, Aug. 28, 2006, vol. 174, No. 5, 689-700.

* cited by examiner

SEQUENCE LISTING

```
<160> NUMBER OF SEQ ID NOS: 22

<210> SEQ ID NO 1
<211> LENGTH: 6
<212> TYPE: PRT
<213> ORGANISM: Homo sapiens

<400> SEQUENCE: 1

Lys Ser Ile Val Glu Lys
1               5
```

```
<210> SEQ ID NO 2
<211> LENGTH: 21
<212> TYPE: DNA
<213> ORGANISM: Artificial Sequence
<220> FEATURE:
<223> OTHER INFORMATION: A synthetic siRNA

<400> SEQUENCE: 2
cgacaauaaa cgguacuugt t                                              21

<210> SEQ ID NO 3
<211> LENGTH: 19
<212> TYPE: RNA
<213> ORGANISM: Homo sapiens

<400> SEQUENCE: 3
ggaggaauuc uaugccuga                                                 19

<210> SEQ ID NO 4
<211> LENGTH: 138
<212> TYPE: PRT
<213> ORGANISM: Homo sapiens

<400> SEQUENCE: 4
```

Met Lys Phe Thr Thr Leu Leu Phe Leu Ala Ala Val Ala Gly Ala Leu
 1               5                  10                  15

Val Tyr Ala Glu Asp Ala Ser Ser Asp Ser Thr Gly Ala Asp Pro Ala
                20                  25                  30

Gln Glu Ala Gly Thr Ser Lys Pro Asn Glu Glu Ile Ser Gly Pro Ala
         35                  40                  45

Glu Pro Ala Ser Pro Pro Glu Thr Thr Thr Thr Ala Gln Glu Thr Ser
 50                  55                  60

Ala Ala Ala Val Gln Gly Thr Ala Lys Val Thr Ser Ser Arg Gln Glu
 65                  70                  75                  80

Leu Asn Pro Leu Lys Ser Ile Val Glu Lys Ser Ile Leu Leu Thr Glu
                 85                  90                  95

Gln Ala Leu Ala Lys Ala Gly Lys Gly Met His Gly Val Pro Gly
                100                 105                 110

Gly Lys Gln Phe Ile Glu Asn Gly Ser Glu Phe Ala Gln Lys Leu Leu
        115                 120                 125

Lys Lys Phe Ser Leu Leu Lys Pro Trp Ala
        130                 135

```
<210> SEQ ID NO 5
<211> LENGTH: 21
<212> TYPE: DNA
<213> ORGANISM: Artificial Sequence
<220> FEATURE:
<223> OTHER INFORMATION: A synthetic siRNA

<400> SEQUENCE: 5
ggacuucacc uuugaaacct t                                              21

<210> SEQ ID NO 6
<211> LENGTH: 21
<212> TYPE: DNA
<213> ORGANISM: Artificial Sequence
<220> FEATURE:
<223> OTHER INFORMATION: A synthetic siRNA

<400> SEQUENCE: 6
gguaaguuaa guaaguugat t                                              21
```

```
<210> SEQ ID NO 7
<211> LENGTH: 21
<212> TYPE: DNA
<213> ORGANISM: Artificial Sequence
<220> FEATURE:
<223> OTHER INFORMATION: A synthetic siRNA

<400> SEQUENCE: 7
ggaguuuuau gcguaaaact t                                              21

<210> SEQ ID NO 8
<211> LENGTH: 21
<212> TYPE: DNA
<213> ORGANISM: Artificial Sequence
<220> FEATURE:
<223> OTHER INFORMATION: A synthetic siRNA

<400> SEQUENCE: 8
ggauguagag aguccagagt t                                              21

<210> SEQ ID NO 9
<211> LENGTH: 21
<212> TYPE: DNA
<213> ORGANISM: Artificial Sequence
<220> FEATURE:
<223> OTHER INFORMATION: A synthetic siRNA

<400> SEQUENCE: 9
ggaguguauc cuauugaugt t                                              21

<210> SEQ ID NO 10
<211> LENGTH: 21
<212> TYPE: RNA
<213> ORGANISM: Artificial Sequence
<220> FEATURE:
<223> OTHER INFORMATION: A synthetic siRNA

<400> SEQUENCE: 10
gcaaugaacc uaacaguuuu u                                              21

<210> SEQ ID NO 11
<211> LENGTH: 21
<212> TYPE: RNA
<213> ORGANISM: Artificial Sequence
<220> FEATURE:
<223> OTHER INFORMATION: A synthetic siRNA

<400> SEQUENCE: 11
gaucaaaccu ugccaccuuu u                                              21

<210> SEQ ID NO 12
<211> LENGTH: 310
<212> TYPE: PRT
<213> ORGANISM: Homo sapiens

<400> SEQUENCE: 12

Met Arg Arg Ala Ala Leu Trp Leu Trp Leu Cys Ala Leu Ala Leu Ser
 1               5                  10                  15

Leu Gln Pro Ala Leu Pro Gln Ile Val Ala Thr Asn Leu Pro Pro Glu
                20                  25                  30

Asp Gln Asp Gly Ser Gly Asp Asp Ser Asp Asn Phe Ser Gly Ser Gly
            35                  40                  45

Ala Gly Ala Leu Gln Asp Ile Thr Leu Ser Gln Gln Thr Pro Ser Thr
        50                  55                  60
```

Trp Lys Asp Thr Gln Leu Leu Thr Ala Ile Pro Thr Ser Pro Glu Pro
 65                  70                  75                  80

Thr Gly Leu Glu Ala Thr Ala Ala Ser Thr Ser Thr Leu Pro Ala Gly
                 85                  90                  95

Glu Gly Pro Lys Glu Gly Glu Ala Val Val Leu Pro Glu Val Glu Pro
            100                 105                 110

Gly Leu Thr Ala Arg Glu Gln Glu Ala Thr Pro Arg Pro Arg Glu Thr
        115                 120                 125

Thr Gln Leu Pro Thr Thr His Gln Ala Ser Thr Thr Ala Thr Thr
130                 135                 140

Ala Gln Glu Pro Ala Thr Ser His Pro His Arg Asp Met Gln Pro Gly
145                 150                 155                 160

His His Glu Thr Ser Thr Pro Ala Gly Pro Ser Gln Ala Asp Leu His
                165                 170                 175

Thr Pro His Thr Glu Asp Gly Gly Pro Ser Ala Thr Glu Arg Ala Ala
            180                 185                 190

Glu Asp Gly Ala Ser Ser Gln Leu Pro Ala Ala Glu Gly Ser Gly Glu
        195                 200                 205

Gln Asp Phe Thr Phe Glu Thr Ser Gly Glu Asn Thr Ala Val Val Ala
210                 215                 220

Val Glu Pro Asp Arg Arg Asn Gln Ser Pro Val Asp Gln Gly Ala Thr
225                 230                 235                 240

Gly Ala Ser Gln Gly Leu Leu Asp Arg Lys Glu Val Leu Gly Gly Val
                245                 250                 255

Ile Ala Gly Gly Leu Val Gly Leu Ile Phe Ala Val Cys Leu Val Gly
            260                 265                 270

Phe Met Leu Tyr Arg Met Lys Lys Lys Asp Glu Gly Ser Tyr Ser Leu
        275                 280                 285

Glu Glu Pro Lys Gln Ala Asn Gly Gly Ala Tyr Gln Lys Pro Thr Lys
290                 295                 300

Gln Glu Glu Phe Tyr Ala
305                 310

<210> SEQ ID NO 13
<211> LENGTH: 543
<212> TYPE: PRT
<213> ORGANISM: Homo sapiens

<400> SEQUENCE: 13

Met Leu Leu Arg Ser Lys Pro Ala Leu Pro Pro Pro Leu Met Leu Leu
  1               5                  10                  15

Leu Leu Gly Pro Leu Gly Pro Leu Ser Pro Gly Ala Leu Pro Arg Pro
                 20                  25                  30

Ala Gln Ala Gln Asp Val Val Asp Leu Asp Phe Phe Thr Gln Glu Pro
            35                  40                  45

Leu His Leu Val Ser Pro Ser Phe Leu Ser Val Thr Ile Asp Ala Asn
        50                  55                  60

Leu Ala Thr Asp Pro Arg Phe Leu Ile Leu Gly Ser Pro Lys Leu
 65                 70                  75                  80

Arg Thr Leu Ala Arg Gly Leu Ser Pro Ala Tyr Leu Arg Phe Gly Gly
                 85                  90                  95

Thr Lys Thr Asp Phe Leu Ile Phe Asp Pro Lys Lys Glu Ser Thr Phe
            100                 105                 110

Glu Glu Arg Ser Tyr Trp Gln Ser Gln Val Asn Gln Asp Ile Cys Lys
        115                 120                 125

-continued

```
Tyr Gly Ser Ile Pro Pro Asp Val Glu Glu Lys Leu Arg Leu Glu Trp
    130                 135                 140

Pro Tyr Gln Glu Gln Leu Leu Leu Arg Glu His Tyr Gln Lys Lys Phe
145                 150                 155                 160

Lys Asn Ser Thr Tyr Ser Arg Ser Ser Val Asp Val Leu Tyr Thr Phe
                    165                 170                 175

Ala Asn Cys Ser Gly Leu Asp Leu Ile Phe Gly Leu Asn Ala Leu Leu
            180                 185                 190

Arg Thr Ala Asp Leu Gln Trp Asn Ser Ser Asn Ala Gln Leu Leu Leu
        195                 200                 205

Asp Tyr Cys Ser Ser Lys Gly Tyr Asn Ile Ser Trp Glu Leu Gly Asn
    210                 215                 220

Glu Pro Asn Ser Phe Leu Lys Lys Ala Asp Ile Phe Ile Asn Gly Ser
225                 230                 235                 240

Gln Leu Gly Glu Asp Phe Ile Gln Leu His Lys Leu Leu Arg Lys Ser
                    245                 250                 255

Thr Phe Lys Asn Ala Lys Leu Tyr Gly Pro Asp Val Gly Gln Pro Arg
            260                 265                 270

Arg Lys Thr Ala Lys Met Leu Lys Ser Phe Leu Lys Ala Gly Gly Glu
        275                 280                 285

Val Ile Asp Ser Val Thr Trp His His Tyr Tyr Leu Asn Gly Arg Thr
    290                 295                 300

Ala Thr Lys Glu Asp Phe Leu Asn Pro Asp Val Leu Asp Ile Phe Ile
305                 310                 315                 320

Ser Ser Val Gln Lys Val Phe Gln Val Val Glu Ser Thr Arg Pro Gly
                    325                 330                 335

Lys Lys Val Trp Leu Gly Glu Thr Ser Ser Ala Tyr Gly Gly Gly Ala
            340                 345                 350

Pro Leu Leu Ser Asp Thr Phe Ala Ala Gly Phe Met Trp Leu Asp Lys
        355                 360                 365

Leu Gly Leu Ser Ala Arg Met Gly Ile Glu Val Val Met Arg Gln Val
    370                 375                 380

Phe Phe Gly Ala Gly Asn Tyr His Leu Val Asp Glu Asn Phe Asp Pro
385                 390                 395                 400

Leu Pro Asp Tyr Trp Leu Ser Leu Leu Phe Lys Lys Leu Val Gly Thr
                    405                 410                 415

Lys Val Leu Met Ala Ser Val Gln Gly Ser Lys Arg Arg Lys Leu Arg
            420                 425                 430

Val Tyr Leu His Cys Thr Asn Thr Asp Asn Pro Arg Tyr Lys Glu Gly
        435                 440                 445

Asp Leu Thr Leu Tyr Ala Ile Asn Leu His Asn Val Thr Lys Tyr Leu
    450                 455                 460

Arg Leu Pro Tyr Pro Phe Ser Asn Lys Gln Val Asp Lys Tyr Leu Leu
465                 470                 475                 480

Arg Pro Leu Gly Pro His Gly Leu Leu Ser Lys Ser Val Gln Leu Asn
                    485                 490                 495

Gly Leu Thr Leu Lys Met Val Asp Asp Gln Thr Leu Pro Pro Leu Met
            500                 505                 510

Glu Lys Pro Leu Arg Pro Gly Ser Ser Leu Gly Leu Pro Ala Phe Ser
        515                 520                 525

Tyr Ser Phe Phe Val Ile Arg Asn Ala Lys Val Ala Ala Cys Ile
    530                 535                 540
```

```
<210> SEQ ID NO 14
<211> LENGTH: 21
<212> TYPE: RNA
<213> ORGANISM: Artificial Sequence
<220> FEATURE:
<223> OTHER INFORMATION: A synthetic siRNA

<400> SEQUENCE: 14
ggacuggacu ugaucuuugu u                                              21

<210> SEQ ID NO 15
<211> LENGTH: 21
<212> TYPE: RNA
<213> ORGANISM: Artificial Sequence
<220> FEATURE:
<223> OTHER INFORMATION: A synthetic siRNA

<400> SEQUENCE: 15
gaacagcacc uacucaagau u                                              21

<210> SEQ ID NO 16
<211> LENGTH: 36
<212> TYPE: DNA
<213> ORGANISM: Artificial Sequence
<220> FEATURE:
<223> OTHER INFORMATION: A synthetic primer

<400> SEQUENCE: 16
ggtggtggat ccacgcagct cctgacggct attccc                              36

<210> SEQ ID NO 17
<211> LENGTH: 36
<212> TYPE: DNA
<213> ORGANISM: Artificial Sequence
<220> FEATURE:
<223> OTHER INFORMATION: A synthetic primer

<400> SEQUENCE: 17
ggtggtggat cccaggctca gcgccagcgc gcacag                              36

<210> SEQ ID NO 18
<211> LENGTH: 29
<212> TYPE: DNA
<213> ORGANISM: Artificial Sequence
<220> FEATURE:
<223> OTHER INFORMATION: A synthetic primer

<400> SEQUENCE: 18
ctagctagct tgcaaagcac ctgcacctg                                      29

<210> SEQ ID NO 19
<211> LENGTH: 27
<212> TYPE: DNA
<213> ORGANISM: Artificial Sequence
<220> FEATURE:
<223> OTHER INFORMATION: A synthetic primer

<400> SEQUENCE: 19
ctagctagcg aggtgctggg aggggtc                                        27

<210> SEQ ID NO 20
<211> LENGTH: 29
<212> TYPE: DNA
<213> ORGANISM: Artificial Sequence
<220> FEATURE:
<223> OTHER INFORMATION: A synthetic primer

<400> SEQUENCE: 20
```

```
ctatagggag acccaagctt ggtaccgag                                29

<210> SEQ ID NO 21
<211> LENGTH: 25
<212> TYPE: DNA
<213> ORGANISM: Artificial Sequence
<220> FEATURE:
<223> OTHER INFORMATION: A synthetic primer

<400> SEQUENCE: 21
ccggaattca gcacctgcac ctgag                                    25

<210> SEQ ID NO 22
<211> LENGTH: 11
<212> TYPE: PRT
<213> ORGANISM: Homo sapiens

<400> SEQUENCE: 22

Ser Ile Val Glu Lys Ser Ile Leu Leu Thr Glu
 1               5                  10
```

LACRITIN-SYNDECAN FUSION PROTEINS

RELATED APPLICATIONS

This application claims priority from U.S. Provisional Application Ser. No. 60/994,090, filed Sep. 17, 2007, titled Lacritin-Syndecan Interactions, which application is herein incorporated in its entirety by reference.

This application is also related to U.S. Pat. No. 7,320,870; U.S. application Ser. No. 10/468,372 which published as 20040081984 on Apr. 29, 2004; U.S. application Ser. No. 11/596,506 which published as 20070207522 on Sep. 6, 2007 and WO 2008/033477, which patent, applications and publications are herein incorporated in their entirety by referenced.

US GOVERNMENT RIGHTS

This invention was made with United States Government support under Grant No. R01 EY13143, awarded by National Institutes of Health. The United States Government has certain rights in the invention.

BACKGROUND

Cell surface proteoglycans are key players in epithelial morphogenesis. They form gradients that immobilize mitogens in proximity to signaling receptors (Wang and Laurie, 2004; Häcker et al., 2005; Radtke and Clevers, 2005), contribute to cellular adhesion by ligating the extracellular matrix (ECM) and at least in one case participate in integrin coupling (Beauvais et al., 2004; McQuade et al., 2006). Cell surface proteoglycans consist of a core protein and associated glycosaminoglycan chains, mainly heparan sulfate (HS). Current dogma states that mitogen, cytokine and ECM binding is largely the domain of the anionic HS chains (Couchman 2003; Häcker et al., 2005). HS chains are generated by a complement of Golgi polymerases, epimerase, and sulphotransferases during post-translational modification. Each is thought to vary in relative activity by cell or tissue type (Perrimon and Bernfield, 2000). Thus within a given epithelium or endothelium, a structurally similar HS chain can be attached to genetically distinct core protein (Zako et al., 2003).

New work has shed light on how HS proteoglycan specificity is generated in development and disease. Most involve extracellular enzymes that affect cell surface HS proteoglycans in unexpected ways. Removal of certain HS 6-O-sulfates by endo-6-O-sulfatases Sulf1 and Sulf2 disrupts the binding of the BMP inhibitor Noggin, leading to its dispersal and establishment of BMP signaling (Viviano et al., 2004). In contrast, this same HS modification diminishes FGF binding and assembly with its signaling receptor (Dai et al., 2005). In another extracellular modification mechanism, HS cleavage by heparanase generates soluble fragments of HS that form complexes of FGF-HS and trigger cellular proliferation, migration, and angiogenesis (Kato et al., 1998). In another mechanism, matrix metalloproteinase-7-dependent shedding of the entire syndecan ectodomain promotes cancer-associated upregulation of glypican-1 and tumor growth (Ding et al., 2005).

In addition to its HS-dependent signaling mechanisms, recent work has shown that the syndecan core proteins themselves participate as cell surface receptors. Their extracellular protein domains regulate the activation of integrins (Beauvais et al. 2003; Beauvais et al., 2004; McQuade et al. 2006), bind growth factors, including Wnt, midkine and pleitrophin (Capurro et al, 2005; Deepa et al. 2004), and disrupt carcinoma activity when added as recombinant competitors, presumably by disrupting their assembly with other signaling receptors at the cell surface.

There is a long felt need in the art for methods and compositions to identify and regulate the signaling pathways of lacritin and syndecan. The present invention satisfies these needs.

SUMMARY OF THE INVENTION

Here we report on a novel mechanism of syndecan-1 (SDC1) signaling that relies on a direct binding interaction of the extracellular core protein domain of the syndecan and modification of the proteoglycan by HS-modifying enzyme. The mechanism involves the partially characterized prosecretory mitogen lacritin discovered as a consequence of a search for epithelial differentiation factors (Sanghi et al., 2001). Lacritin is a small (12.3 kDa) epithelial-selective human glycoprotein secreted in tear protein (accession Q9GZZ8). Lacritin signals to STIM1, mTOR and NFATC1 via rapid PKCα dephosphorylation and PLD activation (Wang et al., 2006) to potentially regulate differentiation, renewal and secretion by the non-germative exocrine epithelia that it preferentially targets. With the exception of pancreatic β-cells (Dor et al., 2004), mechanisms of non-germative epithelial differentiation and renewal are poorly understood. Lacritin deletion analysis identified a C-terminal mitogenic domain with amphipathic alpha-helical structure (Wang et al., 2006) common to many ligand-receptor or ligand-ligand binding sites (Barden et al, 1997; Siemeister et al., 1998). We report here that lacritin's C-terminus targets the SDC1 core protein as a prerequisite for mitogenesis. A second and novel prerequisite is prior modification or removal of HS from the syndecan by heparanase-1. We postulate that the localized action of heparanase converts a widely expressed cell surface proteoglycan into a localized lacritin-binding protein that is required for mitogenic signaling.

The present invention is based on the discovery that lacritin interacts with syndecan, as well as novel regulation of syndecan. The present invention is directed to the regulation of lacritin-syndecan interactions and the associated signal transduction pathway and events and processes regulated by this pathway. In one aspect, regulation of the pathway is useful to promote ocular cell survival, and more particularly to promote ocular cell survival in the presence of an environmental insult. The invention is also directed to the use of lacritin to prevent and treat corneal infections and inflammation. The invention is further directed to the use of lacritin to promote corneal wound repair following environmental insult or surgical procedures of the cornea. The invention is also directed to the use of lacritin as a mitogen for only specific epithelial cells.

In one aspect, the invention encompasses a composition for treating or preventing a disease, disorder, or condition which is regulated or effected by lacritin via a lacritin-syndecan interaction and signaling pathway as described herein. In one aspect, the signaling pathways are PKC-α-dependent NFAT and mTOR pathways. In one aspect, the compounds comprise siRNA.

Lacritin is a selective mitogen for only certain epithelial cells. In one embodiment, the invention provides a method of inducing proliferation of epithelial cells which are sensitive to induction of proliferation by lacritin and fragments, derivatives, and homologs thereof.

In one aspect, proliferation can be inhibited or blocked using methods to inhibit lacritin, to inhibit lacritin-syndecan interaction, and by inhibiting the downstream signaling pathway induced by lacritin-syndecan interactions (for example, with siRNA).

In one aspect, proliferation can be stimulated by stimulating or enhancing lacritin, lacritin-syndecan interaction, syndecan modification, and by stimulating the downstream signaling pathway induced by lacritin-syndecan interactions.

In one embodiment, the present invention provides methods and compositions for regulating or modifying syndecan to modulate its interaction and binding with lacritin. In one aspect, the invention provides methods and compositions for heparanase modification of syndecan. In one aspect, the entire heparan sulfate moiety is removed. In another aspect, the invention provides methods and compositions for deglycanating syndecan.

One aspect provides a fusion protein comprising syndecan-1 and lacritin. In one embodiment only the N-terminal portion of syndecan-1 is present in a fusion protein with lacritin, for example, amino acids 1-51 of syndecan (the fusion protein is prepared by methods available to those of skill in the art (including recombinant techniques), as an example, the preparation of a fusion protein is outlined in FIG. 16). Thus, heparanase or other factors would not be needed for the interaction of lacritin and syndecan. This fusion protein can be used in any of the methods described herein including epithelial proliferation, protection against inflammation and aid in wound healing after an injury or an insult to the eye (e.g., laser eye surgery including lasik surgery and photorefractive keratectomy (PRK)) or in preventing injury or insult to the eye (e.g., prior to eye surgery).

In one embodiment, methods and compositions useful for regulating heparanase are encompassed within the invention.

In one embodiment, the present invention provides methods and compositions for targeting the binding/interaction regions of lacritin and syndecan as described herein. In one aspect, the domain on lacritin is at about amino acid residues 100 and 109.

In another embodiment, the invention provides a method of treating or preventing diseases, disorders, or conditions in a subject in need thereof by methods and compositions encompassed within the present invention.

The invention further provides a kit for administering the compositions of the invention.

Various aspects and embodiments of the invention are described in further detail below.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

Abbreviations and Acronyms

Figure 1A:
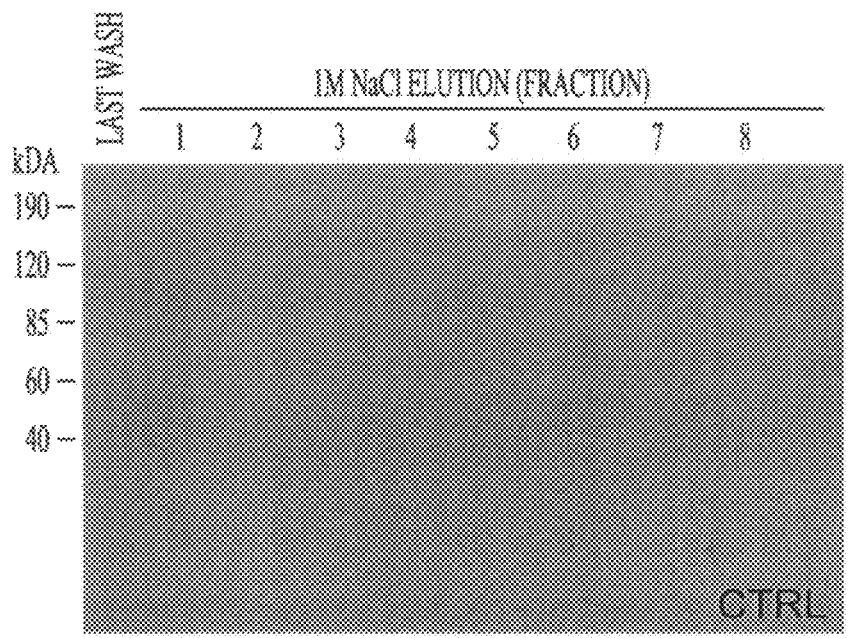
FIG. 1. Lacritin affinity purification of cell surface SDC1. Detergent lysates of surface biotinylated HSG cells were incubated overnight in detergent and physiological salt with intein-chitin columns either lacking (A) or containing (B) lacritin. After extensive washing in the same buffer, the columns were eluted with 1 M NaCl and eluted proteins were identified by blotting with streptavidin-peroxidase. A predominant 190 kDa biotinylated protein eluting from the lacritin column was identified by mass spectrometry as human SDC1.

FACS means fluorescence activated cell sorter
HCE means human corneal epithelial
HS means heparan sulfate
HSG means human salivary gland
IRB means institutional review board
SDC1 means syndecan-1

Definitions

In describing and claiming the invention, the following terminology will be used in accordance with the definitions set forth below.

The articles "a" and "an" are used herein to refer to one or to more than one (i.e., to at least one) of the grammatical object of the article. By way of example, "an element" means one element or more than one element.

As used herein, amino acids are represented by the full name thereof, by the three letter code corresponding thereto, or by the one-letter code corresponding thereto, as indicated in the following table:

| Full Name | Three-Letter Code | One-Letter Code |
|---|---|---|
| Aspartic Acid | Asp | D |
| Glutamic Acid | Glu | E |
| Lysine | Lys | K |
| Arginine | Arg | R |
| Histidine | His | H |
| Tyrosine | Tyr | Y |
| Cysteine | Cys | C |
| Asparagine | Asn | N |
| Glutamine | Gln | Q |
| Serine | Ser | S |
| Threonine | Thr | T |

| Full Name | Three-Letter Code | One-Letter Code |
|---|---|---|
| Glycine | Gly | G |
| Alanine | Ala | A |
| Valine | Val | V |
| Leucine | Leu | L |
| Isoleucine | Ile | I |
| Methionine | Met | M |
| Proline | Pro | P |
| Phenylalanine | Phe | F |
| Tryptophan | Trp | W |

The expression "amino acid" as used herein is meant to include both natural and synthetic amino acids, and both D and L amino acids. "Standard amino acid" means any of the twenty standard L-amino acids commonly found in naturally occurring peptides. "Nonstandard amino acid residue" means any amino acid, other than the standard amino acids, regardless of whether it is prepared synthetically or derived from a natural source. As used herein, "synthetic amino acid" also encompasses chemically modified amino acids, including but not limited to salts, amino acid derivatives (such as amides), and substitutions. Amino acids contained within the peptides of the present invention, and particularly at the carboxy- or amino-terminus, can be modified by methylation, amidation, acetylation or substitution with other chemical groups which can change the peptide's circulating half-life without adversely affecting their activity. Additionally, a disulfide linkage may be present or absent in the peptides of the invention.

The term "amino acid" is used interchangeably with "amino acid residue," and may refer to a free amino acid and to an amino acid residue of a peptide. It will be apparent from the context in which the term is used whether it refers to a free amino acid or a residue of a peptide.

Amino acids have the following general structure:

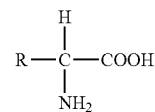

Amino acids may be classified into seven groups on the basis of the side chain R: (1) aliphatic side chains, (2) side chains containing a hydroxylic (OH) group, (3) side chains containing sulfur atoms, (4) side chains containing an acidic or amide group, (5) side chains containing a basic group, (6) side chains containing an aromatic ring, and (7) proline, an imino acid in which the side chain is fused to the amino group.

The nomenclature used to describe the peptide compounds of the present invention follows the conventional practice wherein the amino group is presented to the left and the carboxy group to the right of each amino acid residue. In the formulae representing selected specific embodiments of the present invention, the amino- and carboxy-terminal groups, although not specifically shown, will be understood to be in the form they would assume at physiologic pH values, unless otherwise specified.

The term "basic" or "positively charged" amino acid as used herein, refers to amino acids in which the R groups have a net positive charge at pH 7.0, and include, but are not limited to, the standard amino acids lysine, arginine, and histidine.

The term "antibody," as used herein, refers to an immunoglobulin molecule which is able to specifically bind to a specific epitope on an antigen. Antibodies can be intact immunoglobulins derived from natural sources or from recombinant sources and can be immunoreactive portions of intact immunoglobulins. Antibodies are typically tetramers of immunoglobulin molecules. The antibodies in the present invention may exist in a variety of forms including, for example, polyclonal antibodies, monoclonal antibodies, Fv, Fab and F(ab)2, as well as single chain antibodies and humanized antibodies.

"Antimicrobial agent," as used herein, refers to any compound which impedes the growth of any microbes, or kills such microbes.

As used herein, the term "antisense oligonucleotide" or antisense nucleic acid means a nucleic acid polymer, at least a portion of which is complementary to a nucleic acid which is present in a normal cell or in an affected cell. "Antisense" refers particularly to the nucleic acid sequence of the non-coding strand of a double stranded DNA molecule encoding a protein, or to a sequence which is substantially homologous to the non-coding strand. As defined herein, an antisense sequence is complementary to the sequence of a double stranded DNA molecule encoding a protein. It is not necessary that the antisense sequence be complementary solely to the coding portion of the coding strand of the DNA molecule. The antisense sequence may be complementary to regulatory sequences specified on the coding strand of a DNA molecule encoding a protein, which regulatory sequences control expression of the coding sequences. The antisense oligonucleotides of the invention include, but are not limited to, phosphorothioate oligonucleotides and other modifications of oligonucleotides.

As used herein, the terms "complementary" or "complementarity" are used in reference to polynucleotides (i.e., a sequence of nucleotides) related by the base-pairing rules. For example, for the sequence "A-G-T," is complementary to the sequence "T-C-A."

The terms "detect" and "identify" are used interchangeably herein.

As used herein, a "detectable marker" or a "reporter molecule" is an atom or a molecule that permits the specific detection of a compound comprising the marker in the presence of similar compounds without a marker. Detectable markers or reporter molecules include, e.g., radioactive isotopes, antigenic determinants, enzymes, nucleic acids available for hybridization, chromophores, fluorophores, chemiluminescent molecules, electrochemically detectable molecules, and molecules that provide for altered fluorescence polarization or altered light scattering.

An "enhancer" is a DNA regulatory element that can increase the efficiency of transcription, regardless of the distance or orientation of the enhancer relative to the start site of transcription.

As used herein, the phrase "enhancing survival" refers to decreasing the amount of death, or the rate of death, in a cell population. Enhancing survival can be due to preventing cell death alone (e.g., cell death in conjunction with apoptosis), or decreasing the rate of cell death. The decrease in cell death can also result from indirect effects such as inducing proliferation of some cells, such indirect effect effectively replenishing at least some or all of a population of cells as they die. Enhancing survival of cells can also be accomplished by a combination of inducing proliferation and decreasing cell death, or the rate of cell death. "Promoting survival" and "enhancing survivability" are used interchangeably with "enhancing survival" herein.

A "fragment" or "segment" is a portion of an amino acid sequence, comprising at least one amino acid, or a portion of a nucleic acid sequence comprising at least one nucleotide.

The terms "fragment" and "segment" are used interchangeably herein. A fragment of a lacritin peptide which is used herein as part of a composition for use in a treatment or to elicit a lacritin effect, is presumed to be a biologically active fragment for the response to be elicited.

As used herein, a "functional" biological molecule is a biological molecule in a form in which it exhibits a property or activity by which it is characterized. A functional enzyme, for example, is one which exhibits the characteristic catalytic activity by which the enzyme is characterized.

As used herein, a "gene" refers to the nucleic acid coding sequence as well as the regulatory elements necessary for the DNA sequence to be transcribed into messenger RNA (mRNA) and then translated into a sequence of amino acids characteristic of a specific polypeptide.

"Homologous" as used herein, refers to the subunit sequence similarity between two polymeric molecules, e.g., between two nucleic acid molecules, e.g., two DNA molecules or two RNA molecules, or between two polypeptide molecules. When a subunit position in both of the two molecules is occupied by the same monomeric subunit, e.g., if a position in each of two DNA molecules is occupied by adenine, then they are homologous at that position. The homology between two sequences is a direct function of the number of matching or homologous positions, e.g., if half (e.g., five positions in a polymer ten subunits in length) of the positions in two compound sequences are homologous then the two sequences are 50% homologous, if 90% of the positions, e.g., 9 of 10, are matched or homologous, the two sequences share 90% homology. By way of example, the DNA sequences 3'ATTGCC5' and 3'TATGGC share 50% homology.

As used herein, "homology" is used synonymously with "identity."

The determination of percent identity between two nucleotide or amino acid sequences can be accomplished using a mathematical algorithm. For example, a mathematical algorithm useful for comparing two sequences is the algorithm of Karlin and Altschul (1990, Proc. Natl. Acad. Sci. USA 87:2264-2268), modified as in Karlin and Altschul (1993, Proc. Natl. Acad. Sci. USA 90:5873-5877). This algorithm is incorporated into the NBLAST and XBLAST programs of Altschul, et al. (1990, J. Mol. Biol. 215:403-410), and can be accessed, for example at the National Center for Biotechnology Information (NCBI) world wide web site. BLAST nucleotide searches can be performed with the NBLAST program (designated "blastn" at the NCBI web site), using the following parameters: gap penalty=5; gap extension penalty=2; mismatch penalty=3; match reward=1; expectation value 10.0; and word size=11 to obtain nucleotide sequences homologous to a nucleic acid described herein. BLAST protein searches can be performed with the XBLAST program (designated "blastn" at the NCBI web site) or the NCBI "blastp" program, using the following parameters: expectation value 10.0, BLOSUM62 scoring matrix to obtain amino acid sequences homologous to a protein molecule described herein. To obtain gapped alignments for comparison purposes, Gapped BLAST can be utilized as described in Altschul et al. (1997, Nucleic Acids Res. 25:3389-3402). Alternatively, PSI-Blast or PHI-Blast can be used to perform an iterated search which detects distant relationships between molecules (Id.) and relationships between molecules which share a common pattern. When utilizing BLAST, Gapped BLAST, PSI-Blast, and PHI-Blast programs, the default parameters of the respective programs (e.g., XBLAST and NBLAST) can be used.

The percent identity between two sequences can be determined using techniques similar to those described above, with or without allowing gaps. In calculating percent identity, typically exact matches are counted.

As used herein, the term "insult" refers to contact with a substance or environmental change that results in an alteration of normal cellular metabolism in a cell or population of cells. Environmental insults may include, but are not limited to, chemicals, environmental pollutants, heavy metals, viral or bacterial infections, changes in temperature, changes in pH, as well as agents producing oxidative damage, DNA damage, or pathogenesis. The term "insult" is used interchangeably with "environmental insult" herein.

An "isolated nucleic acid" refers to a nucleic acid segment or fragment which has been separated from sequences which flank it in a naturally occurring to state, e.g., a DNA fragment which has been removed from the sequences which are normally adjacent to the fragment, e.g., the sequences adjacent to the fragment in a genome in which it naturally occurs. The term also applies to nucleic acids which have been substantially purified from other components which naturally accompany the nucleic acid, e.g., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (e.g., as a cDNA or a genomic or cDNA fragment produced by PCR or restriction enzyme digestion) independent of other sequences. It also includes a recombinant DNA which is part of a hybrid gene encoding additional polypeptide sequence.

As used herein, the term "lacritin polypeptide" and like terms refers to peptides comprising the amino acid sequence of SEQ ID NO: 4 and biologically active fragments, derivatives, and homologs thereof. As used herein, the term "biologically active fragments" or "bioactive fragment" of a lacritin polypeptide encompasses natural or synthetic portions of the amino acid sequence

```
MKFTTLLFLAAVAGALVYAEDASSDSTGADPAQEAGTSKPNEEI

SGPAEPASPPETTTTAQETSAAAVQGTAKVTSSRQELNPLKSIV

EKSILLTEQALAKAGKGMHGGVPGGKQFIENGSEFAQKLLKKFS

LLKPWA (SEQ ID NO: 4).
```

As used herein, the term "syndecan-1" refers to peptides comprising the amino acid sequence of SEQ ID NO:12 and biologically active fragments, derivatives, and homologs thereof. As used herein, the term "biologically active fragments" or "bioactive fragment" of a syndecan-1 polypeptide encompasses natural or synthetic portions of the amino acid sequence

```
MRRAALWLWLCALALSLQPALPQIVATNLPPEDQDGSGDDSDNF

SGSGAGALQDITLSQQTPSTWKDTQLLTAIPTSPEPTGLEATAA

STSTLPAGEGPKEGEAVVLPEVEPGLTAREQEATPRPRETTQLP

TTHQASTTTATTAQEPATSHPHRDMQPGHHETSTPAGPSQADLH

TPHTEDGGPSATERAAEDGASSQLPAAEGSGEQDFTFETSGENT

AVVAVEPDRRNQSPVDQGATGASQGLLDRKEVLGGVIAGGLVGL

IFAVCLVGFMLYRMKKKDEGSYSLEEPKQANGGAYQKPTKQEEF

YA (SEQ ID NO: 12).
```

As used herein, the term "heparanase" refers to peptides comprising the amino acid sequence of SEQ ID NO:13 and biologically active fragments, derivatives, and homologs thereof. As used herein, the term "biologically active fragments" or "bioactive fragment" of a heparanase polypeptide encompasses natural or synthetic portions of the amino acid sequence

```
MLLRSKPALPPPLMLLLLGPLGPLSPGALPRPAQAQDVVDLDFF

TQEPLHLVSPSFLSVTIDANLATDPRFLILLGSPKLRTLARGLS

PAYLRFGGTKTDFLIFDPKKESTFEERSYWQSQVNQDICKYGSI

PPDVEEKLRLEWPYQEQLLLREHYQKKFKNSTYSRSSVDVLYTF

ANCSGLDLIFGLNALLRTADLQWNSSNAQLLLDYCSSKGYNISW

ELGNEPNSFLKKADIFINGSQLGEDFIQLHKLLRKSTFKNAKLY

GPDVGQPRRKTAKMLKSFLKAGGEVIDSVTWHHYYLNGRTATKE

DFLNPDVLDIFISSVQKVFQVVESTRPGKKVWLGETSSAYGGGA

PLLSDTFAAGFMWLDKLGLSARMGIEVVMRQVFFGAGNYHLVDE

NFDPLPDYWLSLLFKKLVGTKVLMASVQGSKRRKLRVYLHCTNT

DNPRYKEGDLTLYAINLHNVTKYLRLPYPFSNKQVDKYLLRPLG

PHGLLSKSVQLNGLTLKMVDDQTLPPLMEKPLRPGSSLGLPAFS

YSFFVIRNAKVAACI (SEQ ID NO: 13).
```

As used herein, a "ligand" is a compound that specifically binds to a target compound. A ligand (e.g., an antibody) "specifically binds to" or "is specifically immunoreactive with" a compound when the ligand functions in a binding reaction which is determinative of the presence of the compound in a sample of heterogeneous compounds. Thus, under designated assay (e.g., immunoassay) conditions, the ligand binds preferentially to a particular compound and does not bind to a significant extent to other compounds present in the sample. For example, an antibody specifically binds under immunoassay conditions to an antigen bearing an epitope against which the antibody was raised. A variety of immunoassay formats may be used to select antibodies specifically immunoreactive with a particular antigen. For example, solid-phase ELISA immunoassays are routinely used to select monoclonal antibodies specifically immunoreactive with an antigen. See Harlow and Lane, 1988, Antibodies, A Laboratory Manual, Cold Spring Harbor Publications, New York, for a description of immunoassay formats and conditions that can be used to determine specific immunoreactivity.

As used herein, the term "linkage" refers to a connection between two groups. The connection can be either covalent or non-covalent, including but not limited to ionic bonds, hydrogen bonding, and hydrophobic/hydrophilic interactions.

As used herein, the term "linker" refers to a molecule that joins two other molecules either covalently or noncovalently, e.g., through ionic or hydrogen bonds or van der Waals interactions.

"Ocular surface," as used herein, refers to the surface of the eye, particularly the corneal surface.

The phrase "ocular surface-associated disease, disorder, or condition," as used herein, refers to any disease, disorder or condition which directly or indirectly causes, or can cause, any of the problems or symptoms described herein regarding disease, disorders, or conditions of the ocular surface.

"Operably linked" refers to a juxtaposition wherein the components are configured so as to perform their usual function. Thus, control sequences or promoters operably linked to a coding sequence are capable of effecting the expression of the coding sequence.

A "marker" is an atom or molecule that permits the specific detection of a molecule comprising that marker in the presence of similar molecules without such a marker. Markers include, for example radioactive isotopes, antigenic determinants, nucleic acids available for hybridization, chromophors, fluorophors, chemiluminescent molecules, electrochemically detectable molecules, molecules that provide for altered fluorescence-polarization or altered light-scattering and molecules that allow for enhanced survival of an cell or organism (i.e. a selectable marker). A reporter gene is a gene that encodes for a marker.

A "polylinker" is a nucleic acid sequence that comprises a series of three or more different restriction endonuclease recognitions sequences closely spaced to one another (i.e. less than 10 nucleotides between each site).

As used herein, the term "promoter/regulatory sequence" means a nucleic acid sequence which is required for expression of a gene product operably linked to the promoter/regulator sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

A "constitutive" promoter is a promoter which drives expression of a gene to which it is operably linked, in a constant manner in a cell. By way of example, promoters which drive expression of cellular housekeeping genes are considered to be constitutive promoters.

An "inducible" promoter is a nucleotide sequence which, when operably linked with a polynucleotide which encodes or specifies a gene product, causes the gene product to be produced in a living cell substantially only when an inducer which corresponds to the promoter is present in the cell.

A "tissue-specific" promoter is a nucleotide sequence which, when operably linked with a polynucleotide which encodes or specifies a gene product, causes the gene product to be produced in a living cell substantially only if the cell is a cell of the tissue type corresponding to the promoter.

As used herein, "nucleic acid," "DNA," and similar terms also include nucleic acid analogs, i.e. analogs having other than a phosphodiester backbone. For example, the so-called "peptide nucleic acids," which are known in the art and have peptide bonds instead of phosphodiester bonds in the backbone, are considered within the scope of the present invention.

As used herein, the term "fragment" as applied to a nucleic acid, may ordinarily be at least about 20 nucleotides in length, typically, at least about 50 nucleotides, more typically, from about 50 to about 100 nucleotides, preferably, at least about 100 to about 200 nucleotides, even more preferably, at least about 200 nucleotides to about 300 nucleotides, yet even more preferably, at least about 300 to about 350, even more preferably, at least about 350 nucleotides to about 500 nucleotides, yet even more preferably, at least about 500 to about 600, even more preferably, at least about 600 nucleotides to about 620 nucleotides, yet even more preferably, at least about 620 to about 650, and most preferably, the nucleic acid fragment will be greater than about 650 nucleotides in length.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

The term "peptide" encompasses a sequence of 3 or more amino acids wherein the amino acids are naturally occurring or synthetic (non-naturally occurring) amino acids. Peptide mimetics include peptides having one or more of the following modifications:

1. peptides wherein one or more of the peptidyl —C(O)NR— linkages (bonds) have been replaced by a non-peptidyl linkage such as a—CH2-carbamate linkage (—CH2OC(O)NR—), a phosphonate linkage, a —CH2-sulfonamide (—CH2—S(O)2NR—) linkage, a urea (—NHC(O)NH—) linkage, a —CH2-secondary amine linkage, or with an alkylated peptidyl linkage (—C(O)NR—) wherein R is C1-C4 alkyl;

2. peptides wherein the N-terminus is derivatized to a —NRR1 group, to a —NRC(O)R group, to a —NRC(O)OR group, to a —NRS(O)2R group, to a —NHC(O)NHR group where R and R1 are hydrogen or C1-C4 alkyl with the proviso that R and R1 are not both hydrogen;

3. peptides wherein the C terminus is derivatized to —C(O)R2 where R2 is selected from the group consisting of C1-C4 alkoxy, and —NR3R4 where R3 and R4 are independently selected from the group consisting of hydrogen and C1-C4 alkyl.

Synthetic or non-naturally occurring amino acids refer to amino acids which do not naturally occur in vivo but which, nevertheless, can be incorporated into the peptide structures described herein. The resulting "synthetic peptide" contain amino acids other than the 20 naturally occurring, genetically encoded amino acids at one, two, or more positions of the peptides. For instance, naphthylalanine can be substituted for tryptophan to facilitate synthesis. Other synthetic amino acids that can be substituted into peptides include L-hydroxypropyl, L-3,4-dihydroxyphenylalanyl, alpha-amino acids such as L-alpha-hydroxylysyl and D-alpha-methylalanyl, L-alpha.-methylalanyl, beta.-amino acids, and isoquinolyl. D amino acids and non-naturally occurring synthetic amino acids can also be incorporated into the peptides. Other derivatives include replacement of the naturally occurring side chains of the 20 genetically encoded amino acids (or any L or D amino acid) with other side chains.

The term "fusion polypeptide" or "fusion protein" refers to a chimeric protein containing a reference protein (e.g., lacritin) joined at the N- and/or C-terminus to one or more heterologous sequences (e.g., a non lacritin polypeptide, such as syndecan). Polypeptide molecules are said to have an "amino terminus" (N terminus) and a "carboxy terminus" (C terminus) because peptide linkages occur between the backbone amino group of a first amino acid residue and the backbone carboxyl group of a second amino acid residue. The terms "N terminal" and "C terminal" in reference to polypeptide sequences refer to regions of polypeptides including portions of the N terminal and C terminal regions of the polypeptide, respectively. A sequence that includes a portion of the N terminal region of polypeptide includes amino acids predominantly from the N terminal half of the polypeptide chain, but is not limited to such sequences. For example, an N terminal sequence may include an interior portion of the polypeptide sequence including bases from both the N terminal and C terminal halves of the polypeptide. The same applies to C terminal regions. N terminal and C terminal regions may, but need not, include the amino acid defining the ultimate N terminus and C terminus of the polypeptide, respectively.

The fusion proteins of the invention may be prepared by recombinant methods or by solid phase chemical peptide synthesis methods. Such methods have been known in the art since the early 1960's (Merrifield, 1963) (See also Stewart et al., Solid Phase Peptide Synthesis, 2 ed., Pierce Chemical Co., Rockford, Ill., pp. 11-12)) and have recently been employed in commercially available laboratory peptide design and synthesis kits (Cambridge Research Biochemicals). Such commercially available laboratory kits have generally utilized the teachings of Geysen et al. (1984) and provide for synthesizing peptides upon the tips of a multitude of "rods" or "pins" all of which are connected to a single plate. When such a system is utilized, a plate of rods or pins is inverted and inserted into a second plate of corresponding wells or reservoirs, which contain solutions for attaching or anchoring an appropriate amino acid to the pin's or rod's tips. By repeating such a process step, e.g., inverting and inserting the rod's and pin's tips into appropriate solutions, amino acids are built into desired peptides. In addition, a number of available FMOC peptide synthesis systems are available. For example, assembly of a polypeptide or fragment can be carried out on a solid support using an Applied Biosystems, Inc. Model 431A automated peptide synthesizer. Such equipment provides ready access to the peptides of the invention, either by direct synthesis or by synthesis of a series of fragments that can be coupled using other known techniques.

The invention also includes a stable cell line that expresses a lacritin/syndecan-1 fusion protein, as well as an expression cassette comprising a nucleic acid molecule encoding the lacritin/syndecan-1 fusion protein, and a vector capable of expressing the nucleic acid molecule of the invention in a host cell. Preferably, the expression cassette comprises a promoter, e.g., a constitutive or regulatable promoter, operably linked to the nucleic acid sequence. In one embodiment, the expression cassette contains an inducible promoter. Also provided is a host cell, e.g., a prokaryotic cell or an eukaryotic cell such as a plant or vertebrate cell, e.g., a mammalian cell, including but not limited to a human, non-human primate, canine, feline, bovine, equine, ovine or rodent (e.g., rabbit, rat, ferret or mouse) cell, which comprises the expression cassette or vector of the invention, and a kit which comprises the nucleic acid molecule, expression cassette, vector, host cell or lacritin/syndecan-1 fusion protein.

As used herein, the term "pharmaceutically acceptable carrier" includes any of the standard pharmaceutical carriers, such as a phosphate buffered saline solution, water, emulsions such as an oil/water or water/oil emulsion, and various types of wetting agents. The term also encompasses any of the agents approved by a regulatory agency of the US Federal government or listed in the US Pharmacopeia for use in animals, including humans.

A "promoter" is a DNA sequence that directs the transcription of a DNA sequence, such as the nucleic acid coding sequence of a gene. Typically, a promoter is located in the 5' region of a gene, proximal to the transcriptional start site of a structural gene. Promoters can be inducible (the rate of transcription changes in response to a specific agent), tissue specific (expressed only in some tissues), temporal specific (expressed only at certain times) or constitutive (expressed in all tissues and at a constant rate of transcription).

A "core promoter" contains essential nucleotide sequences for promoter function, including the TATA box and start of transcription. By this definition, a core promoter may or may not have detectable activity in the absence of specific sequences that enhance the activity or confer tissue specific activity.

As used herein, the term "purified" and like terms relate to the isolation of a molecule or compound in a form that is substantially free of contaminants normally associated with the molecule or compound in a native or natural environment. The term "purified" does not necessarily indicate that complete purity of the particular molecule has been achieved during the process. A "highly purified" compound as used herein refers to a compound that is greater than 90% pure.

A "subject" of experimentation, diagnosis or treatment is an animal, including a human.

The term "substantially pure" describes a compound, e.g., a protein or polypeptide which has been separated from components which naturally accompany it. Typically, a compound is substantially pure when at least 10%, more preferably at least 20%, more preferably at least 50%, more preferably at least 60%, more preferably at least 75%, more preferably at least 90%, and most preferably at least 99% of the total material (by volume, by wet or dry weight, or by mole percent or mole fraction) in a sample is the compound of interest. Purity can be measured by any appropriate method, e.g., in the case of polypeptides by column chromatography, gel electrophoresis, or HPLC analysis. A compound, e.g., a protein, is also substantially purified when it is essentially free of naturally associated components or when it is separated from the native contaminants which accompany it in its natural state.

A "substantially pure nucleic acid", as used herein, refers to a nucleic acid sequence, segment, or fragment which has been purified from the sequences which flank it in a naturally occurring state, e.g., a DNA fragment which has been removed from the sequences which are normally adjacent to the fragment e.g., the sequences adjacent to the fragment in a genome in which it naturally occurs. The term also applies to nucleic acids which have been substantially purified from other components which naturally accompany the nucleic acid, e.g., RNA or DNA or proteins which naturally accompany it in the cell.

A "therapeutic" treatment is a treatment administered to a subject who exhibits signs of pathology for the purpose of diminishing or eliminating those signs.

A "therapeutically effective amount" of a compound is that amount of compound which is sufficient to provide a beneficial effect to the subject to which the compound is administered.

As used herein, the term "treating" includes prophylaxis of the specific disorder or condition, or alleviation of the symptoms associated with a specific disorder or condition and/or preventing or eliminating said symptoms. A "prophylactic" treatment is a treatment administered to a subject who does not exhibit signs of a disease or exhibits only early signs of the disease for the purpose of decreasing the risk of developing pathology associated with the disease. As used herein, the term "treating" includes alleviating the symptoms associated with a specific disease, disorder or condition and/or preventing or eliminating said symptoms.

A "vector" is also meant to include a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, plasmids, cosmids, lambda phage vectors, and the like.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses that incorporate the recombinant polynucleotide.

As used herein, the term "wound" relates to a physical tear or rupture to a tissue or cell layer. A wound may occur by any physical insult, including a surgical procedure.

Embodiments of the Invention

The present invention is directed to uses of a human growth factor-like molecule, "lacritin," and compositions comprising lacritin, or fragments, derivatives, or homologs thereof, and to its interaction with syndecan, and regulation of the pathways effected by such interaction. The invention also encompasses regulation and treatment of diseases, disorders, and conditions by regulating lacritin, lacritin-syndecan interactions, syndecan, and the pathways downstream from lacritin-syndecan interactions. The invention also encompasses use of nucleic acid sequences encoding lacritin, as well as the nucleic acid regulatory elements controlling the expression of lacritin.

The full length 'lacritin' cDNA was previously cloned from a human lacrimal gland library, and the corresponding genomic gene has been cloned and sequenced, including 5.2 kb of upstream and 2.8 kb of downstream genomic sequence.

In one embodiment, the present invention is directed to use of a purified polypeptide comprising the amino acid sequence of SEQ ID NOs: 4, 12 or 13, a bioactive fragment of SEQ ID NOs: 4, 12 or 13, or an amino acid sequence that differs from SEQ ID NOs: 4, 12 or 13 by one or more conservative amino acid substitutions. More preferably, the purified polypeptide comprises an amino acid sequence that differs from SEQ ID NOs: 4, 12 or 13 by 20 or less conservative amino acid substitutions, and more preferably by 10 or less conservative amino acid substitutions. Alternatively, the polypeptide may comprise an amino acid sequence that differs from SEQ ID NOs: 4, 12 or 13 by 1 to 5 alterations, wherein the alterations are independently selected from a single amino acid deletion, insertion, or substitution. Alternatively, the polypeptide comprises an amino acid sequence that is at about 85%, 90%, 95% or 99% identical to SEQ ID NOs: 4, 12 or 13. In one preferred embodiment a composition is provided comprising a polypeptide, selected from the group consisting of SEQ ID NOs: 4, 12 or 13 and a pharmaceutically acceptable carrier. In another preferred embodiment, the polypeptide or fragments thereof are of the mature processed lacritin selected from the group of fragments with up to 25 amino acids deleted from the C-terminus. In another embodiment, up to 25 amino acids are deleted from the N-terminus of SEQ ID NO:4, the full length lacritin.

Physiological experiments recently performed using recombinant lacritin generated by E. coli suggests that lacritin is also a survival factor, i.e., longevity in cell culture was promoted by the addition of physiological amounts of lacritin. Methods for measuring wound healing are known in the art (reviewed in Woo et al., Experimental Eye Research, 80:633-642, 2000). Methods for measuring cell survival are known in the art and include various cellular, molecular, biochemical, and histological techniques.

Lacritin is naturally produced in moderately large quantities by the lacrimal gland for release into the corneal tear film. The therapeutic potential of lacritin, and therefore the lacritin-syndecan interactions in promoting the health of the ocular surface is therefore considerable, particularly as environmental exposure to pollutants and UV exposure increases, and as the proportion of the population, suffering from Dry Eye expands.

The cornea is the main refracting surface of the eye and is vulnerable to environmental hazards or insult including exposure (direct trauma, drying, radiant and ionizing energy), infectious agents (bacteria, viruses—notably herpes simplex and herpes zoster—fungi, and parasites), and inflammation, sometimes in association with systemic dermatologic disorders such as atopic dermatitis, cicatricial pemphigoid, rosacea, and erythema multiforme (Stevens-Johnson syndrome). Bacteria include pseudomonas. Keratitis is an inflammation or infection of the cornea. It is often associated with inflammation of the iris (iritis) or of the uveal tract—the iris, ciliary body, and choroid (uveitis). Keratitis combined with uveitis or iritis is seen commonly in Reiter's disease and occasionally Behcet's disease. Keratitis and uveitis may also occur with herpes simplex infection, in sarcoidosis, and in collagen vascular diseases.

As described above, a host of mediators are implicated in the development and progression of corneal inflammation, such as the proinflammatory cytokines TNF-$\alpha$, IL-1$\beta$, IL-6, and the chemokine IL-8. Also involved are the arachidonic acid-derived eicosanoids which are produced by the activity of cyclooxygenases (primarily PGE2), lipooxygenases (12 (s)-HETE) and cytochrome P450 (12 (r)-HETE). Therefore, in one embodiment of the invention, any method for enhancing lacritin-syndecan interactions and the signals resulting therefrom is useful as an antagonist to inflammatory processes such as those induced or supplemented by proinflammatory agents such as proinflammatory cytokines.

In accordance with one embodiment, a method of reducing or preventing ocular cell death in a mammalian species after contact with an environmental insult, or in response to an ocular-associated disease, disorder, or condition is provided. The method comprises the steps of contacting the cells that have been exposed to the environmental insult to a composition comprising lacritin, or a fragment, derivative, or homolog thereof, as well as methods to enhance lacritin-syndecan interaction. As used herein, cells that are "exposed" to the environmental insult include those cells that have been directly contacted by the environmental insult, as well as those cells that suffer indirectly as a result of direct contact of other cells with the environmental insult. In one embodiment, the ocular cells comprise the corneal epithelial cells. In one embodiment, the exposed cells are contacted with a topically administered ophthalmic formulation comprising a lacritin polypeptide, or a derivative, fragment, or homolog thereof, as well as compounds to enhance lacritin-syndecan interactions.

The lacritin comprising compositions or compositions comprising compounds which enhance lacritin-syndecan interaction of the present invention can be administered prophylactically to promote corneal epithelial cell survival in the presence of common environmental insults such as exposure to UV exposure or pollutants, particularly for those individuals that face excessive exposure to such elements. In another embodiment, the lacritin comprising compositions of the present invention are used to regulate an immune response to inflammation and/or bacterial infection. In another embodiment, a lacritin comprising composition can be administered to aid in the healing process following a surgical procedure to the eye, such as cataract or other vision-corrective surgical procedures. The invention encompasses all surgical procedures of the eye, including laser procedures.

In accordance with one embodiment, a method is provided for treating infections of the eye. The method comprises the step of topically administering a composition comprising a lacritin polypeptide to the eye. In one embodiment, the composition further comprises an anti-microbial agent. Suitable ophthalmic anti-microbial agents are known to those skilled in the art and include those described in U.S. Pat. Nos. 5,300,296, 6,316,669, 6,365,636 and 6,592,907, the disclosures of which are incorporated herein. Examples of anti-microbial agents suitable for use in accordance with the present invention include benzalkonium chloride, benzethonium chloride, benzyl alcohol, chlorobutanol, chlorhexidine digluconate or diacetate, methyl and propyl hydroxybenzoate (parabens), phenylethyl alcohol, phenylmercuric acetate or nitrate, sorbic acid, and thimerosal.

Current tear supplements are not popular with patients, in part because the relief obtained from such products is very brief (less than 15 min). Examples of the tear substitution approach include the use of buffered, isotonic saline solutions, aqueous solutions containing water soluble polymers that render the solutions more viscous and thus less easily shed by the eye. Tear reconstitution is also attempted by providing one or more components of the tear film such as phospholipids and oils. Examples of these treatment approaches are disclosed in U.S. Pat. No. 4,131,651 (Shah et al.), U.S. Pat. No. 4,370,325 (Packman), U.S. Pat. No. 4,409,205 (Shively), U.S. Pat. Nos. 4,744,980 and 4,883,658 (Holly), U.S. Pat. No. 4,914,088 (Glonek), U.S. Pat. No. 5,075,104 (Gressel et al.) and U.S. Pat. No. 5,294,607 (Glonek et al.) the disclosures of which are incorporated herein. Existing ophthalmic formulations may also include TGF-beta, corticosteroids, or androgens. All are non-specific for the eye and have systemic effects. In contrast, lacritin is highly restricted to the eye and is a natural constituent of human tears and the tear film.

An ophthalmic formulation comprising lacritin, or fragments, homologs, or derivatives thereof (for example, an artificial tear fluids containing lacritin), is highly desirable due to the activity of lacritin and its localized effects. In accordance with one embodiment of the invention, compositions comprising lacritin are used to enhance corneal wound healing, and/or treat patients having deficient tear output. The lacritin compositions of the present invention can be formulated using standard ophthalmic components, and preferably, the compositions are formulated as solutions, suspensions, and other dosage forms for topical administration. Aqueous solutions are generally preferred, based on ease of formulation, biological compatibility (especially in view of the malady to be treated, e.g., dry eye-type diseases and disorders), as well as a patient's ability to easily administer such compositions by means of instilling one to two drops of the solutions in the affected eyes. However, the compositions may also be suspensions, viscous or semi-viscous gels, or other types of solid or semi-solid compositions.

The compositions of the present invention may include surfactants, preservative agents, antioxidants, tonicity agents, buffers, preservatives, co-solvents and viscosity building agents. Various surfactants useful in topical ophthalmic formulations may be employed in the present compositions. These surfactants may aid in preventing chemical degradation of lacritin and also prevent the lacritin from binding to the containers in which the compositions are packaged. Examples of surfactants include, but are not limited to: Cremophor® EL, polyoxyl 20 ceto stearyl ether, polyoxyl 40 hydrogenated castor oil, polyoxyl 23 lauryl ether and poloxamer 407 may be used in the compositions. Antioxidants may be added to compositions of the present invention to protect the lacritin polypeptide from oxidation during storage. Examples of such antioxidants include, but are not limited to, vitamin E and analogs thereof, ascorbic acid and derivatives, and butylated hydroxyanisole (BHA).

Existing artificial tears formulations can also be used as pharmaceutically acceptable carriers for the lacritin active agent. Thus in one embodiment, lacritin is used to improve existing artificial tear products for Dry Eye syndromes, as well as develop products to aid corneal wound healing. Examples of artificial tears compositions useful as carriers include, but are not limited to, commercial products, such as Tears Naturale®, Tears Naturale II®, Tears Naturale Free®, and Bion Tears® (Alcon Laboratories, Inc., Fort Worth, Tex.). Examples of other phospholipid carrier formulations include those disclosed in U.S. Pat. No. 4,804,539 (Guo et al.), U.S. Pat. No. 4,883,658 (Holly), U.S. Pat. No. 4,914,088 (Glonek), U.S. Pat. No. 5,075,104 (Gressel et al.), U.S. Pat. No. 5,278,151 (Korb et al.), U.S. Pat. No. 5,294,607 (Glonek et al.), U.S. Pat. No. 5,371,108 (Korb et al.), U.S. Pat. No. 5,578,586 (Glonek et al.); the foregoing patents are incorporated herein by reference to the extent they disclose phospholipid compositions useful as phospholipid carriers of the present invention.

Other compounds may also be added to the ophthalmic compositions of the present invention to increase the viscosity of the carrier. Examples of viscosity enhancing agents include, but are not limited to: polysaccharides, such as hyaluronic acid and its salts, chondroitin sulfate and its salts, dextrans, various polymers of the cellulose family; vinyl polymers; and acrylic acid polymers. In general, the phospholipid carrier or artificial tears carrier compositions will exhibit a viscosity of 1 to 400 centipoises ("cps"). Preferred compositions containing artificial tears or phospholipid carriers and will exhibit a viscosity of about 25 cps.

Topical ophthalmic products are typically packaged in multidose form. Preservatives are thus required to prevent microbial contamination during use. Suitable preservatives include: benzalkonium chloride, chlorobutanol, benzododecinium bromide, methyl paraben, propyl paraben, phenylethyl alcohol, edetate disodium, sorbic acid, polyquaternium-1, or other agents known to those skilled in the art. Such preservatives are typically employed at a level of from 0.001 to 1.0% w/v. Unit dose compositions of the present invention will be sterile, but typically unpreserved. Such compositions, therefore, generally will not contain preservatives.

Because the gene promoter regulating lacritin gene expression is the most specific of any previously described lacrimal gland gene, the regulatory elements of this gene could be used to express other gene products in the eye. In particular, the lacritin gene promoter can be operably linked to a wide variety of exogenous genes to regulate the expression of the gene products to the lacrimal gland and/or used as gene therapy to treat Dry Eye syndromes.

The peptides of the present invention may be readily prepared by standard, well-established techniques, such as solid-phase peptide synthesis (SPPS) as described by Stewart et al. in Solid Phase Peptide Synthesis, 2nd Edition, 1984, Pierce Chemical Company, Rockford, Ill.; and as described by Bodanszky and Bodanszky in The Practice of Peptide Synthesis, 1984, Springer-Verlag, New York. At the outset, a suitably protected amino acid residue is attached through its carboxyl group to a derivatized, insoluble polymeric support, such as cross-linked polystyrene or polyamide resin. "Suitably protected" refers to the presence of protecting groups on both the α-amino group of the amino acid, and on any side chain functional groups. Side chain protecting groups are generally stable to the solvents, reagents and reaction conditions used throughout the synthesis, and are removable under conditions which will not affect the final peptide product. Stepwise synthesis of the oligopeptide is carried out by the removal of the N-protecting group from the initial amino acid, and couple thereto of the carboxyl end of the next amino acid in the sequence of the desired peptide. This amino acid is also suitably protected. The carboxyl of the incoming amino acid can be activated to react with the N-terminus of the support-bound amino acid by formation into a reactive group such as formation into a carbodiimide, a symmetric acid anhydride or an "active ester" group such as hydroxybenzotriazole or pentafluorophenly esters.

Examples of solid phase peptide synthesis methods include the BOC method which utilized tert-butyloxcarbonyl as the α-amino protecting group, and the FMOC method which utilizes 9-fluorenylmethyloxcarbonyl to protect the α-amino of the amino acid residues, both methods of which are well known by those of skill in the art.

Incorporation of N- and/or C-blocking groups can also be achieved using protocols conventional to solid phase peptide synthesis methods. For incorporation of C-terminal blocking groups, for example, synthesis of the desired peptide is typically performed using, as solid phase, a supporting resin that has been chemically modified so that cleavage from the resin results in a peptide having the desired C-terminal blocking group. To provide peptides in which the C-terminus bears a primary amino blocking group, for instance, synthesis is performed using a p-methylbenzhydrylamine (MBHA) resin so that, when peptide synthesis is completed, treatment with hydrofluoric acid releases the desired C-terminally amidated peptide. Similarly, incorporation of an N-methylamine blocking group at the C-terminus is achieved using N-methylaminoethyl-derivatized DVB, resin, which upon HF treatment releases a peptide bearing an N-methylamidated C-terminus. Blockage of the C-terminus by esterification can also be achieved using conventional procedures. This entails use of resin/blocking group combination that permits release of side-chain peptide from the resin, to allow for subsequent reaction with the desired alcohol, to form the ester function. FMOC protecting group, in combination with DVB resin derivatized with methoxyalkoxybenzyl alcohol or equivalent linker, can be used for this purpose, with cleavage from the support being effected by TFA in dicholoromethane. Esterification of the suitably activated carboxyl function e.g. with DCC, can then proceed by addition of the desired alcohol, followed by deprotection and isolation of the esterified peptide product.

Incorporation of N-terminal blocking groups can be achieved while the synthesized peptide is still attached to the resin, for instance by treatment with a suitable anhydride and nitrile. To incorporate an acetyl-blocking group at the N-terminus, for instance, the resin-coupled peptide can be treated with 20% acetic anhydride in acetonitrile. The N-blocked peptide product can then be cleaved from the resin, deprotected and subsequently isolated.

To ensure that the peptide obtained from either chemical or biological synthetic techniques is the desired peptide, analysis of the peptide composition should be conducted. Such amino acid composition analysis may be conducted using high-resolution mass spectrometry to determine the molecular weight of the peptide. Alternatively, or additionally, the amino acid content of the peptide can be confirmed by hydrolyzing the peptide in aqueous acid, and separating, identifying and quantifying the components of the mixture using HPLC, or an amino acid analyzer. Protein sequenators, which sequentially degrade the peptide and identify the amino acids in order, may also be used to determine definitely the sequence of the peptide.

Prior to its use, the peptide is purified to remove contaminants. In this regard, it will be appreciated that the peptide will be purified to meet the standards set out by the appropriate regulatory agencies. Any one of a number of a conventional purification procedures may be used to attain the required level of purity including, for example, reversed-phase high-pressure liquid chromatography (HPLC) using an alkylated silica column such as C4-, C8- or C18-silica. A gradient mobile phase of increasing organic content is generally used to achieve purification, for example, acetonitrile in an aqueous buffer, usually containing a small amount of trifluoroacetic acid. Ion-exchange chromatography can be also used to separate peptides based on their charge.

It will be appreciated, of course, that the peptides or antibodies, derivatives, or fragments thereof may incorporate amino acid residues which are modified without affecting activity. For example, the termini may be derivatized to include blocking groups, i.e. chemical substituents suitable to protect and/or stabilize the N- and C-termini from "undesirable degradation", a term meant to encompass any type of enzymatic, chemical or biochemical breakdown of the compound at its termini which is likely to affect the function of the compound, i.e. sequential degradation of the compound at a terminal end thereof.

Blocking groups include protecting groups conventionally used in the art of peptide chemistry which will not adversely affect the in vivo activities of the peptide. For example, suitable N-terminal blocking groups can be introduced by alkylation or acylation of the N-terminus. Examples of suitable N-terminal blocking groups include $C_1$-$C_5$ branched or unbranched alkyl groups, acyl groups such as formyl and acetyl groups, as well as substituted forms thereof, such as the acetamidomethyl (Acm) group. Desamino analogs of amino acids are also useful N-terminal blocking groups, and can either be coupled to the N-terminus of the peptide or used in place of the N-terminal reside. Suitable C-terminal blocking groups, in which the carboxyl group of the C-terminus is either incorporated or not, include esters, ketones or amides. Ester or ketone-forming alkyl groups, particularly lower alkyl groups such as methyl, ethyl and propyl, and amide-forming amino groups such as primary amines (—$NH_2$), and mono- and di-alkylamino groups such as methylamino, ethylamino, dimethylamino, diethylamino, methylethylamino and the like are examples of C-terminal blocking groups. Descarboxylated amino acid analogues such as agmatine are also useful C-terminal blocking groups and can be either coupled to the peptide's C-terminal residue or used in place of it. Further, it will be appreciated that the free amino and carboxyl groups at the termini can be removed altogether from the peptide to yield desamino and descarboxylated forms thereof without affect on peptide activity.

Other modifications can also be incorporated without adversely affecting the activity and these include, but are not limited to, substitution of one or more of the amino acids in the natural L-isomeric form with amino acids in the D-isomeric form. Thus, the peptide may include one or more D-amino acid resides, or may comprise amino acids which are all in the D-form. Retro-inverso forms of peptides in accordance with the present invention are also contemplated, for example, inverted peptides in which all amino acids are substituted with D-amino acid forms.

Acid addition salts of the present invention are also contemplated as functional equivalents. Thus, a peptide in accordance with the present invention treated with an inorganic acid such as hydrochloric, hydrobromic, sulfuric, nitric, phosphoric, and the like, or an organic acid such as an acetic, propionic, glycolic, pyruvic, oxalic, malic, malonic, succinic, maleic, fumaric, tataric, citric, benzoic, cinnamie, mandelic, methanesulfonic, ethanesulfonic, p-toluenesulfonic, salicyclic and the like, to provide a water soluble salt of the peptide is suitable for use in the invention.

The present invention also provides for analogs of proteins. Analogs can differ from naturally occurring proteins or peptides by conservative amino acid sequence differences or by modifications which do not affect sequence, or by both.

For example, conservative amino acid changes may be made, which although they alter the primary sequence of the protein or peptide, do not normally alter its function. To that end, 10 or more conservative amino acid changes typically have no effect on peptide function. Conservative amino acid substitutions typically include substitutions within the following groups:
glycine, alanine;
valine, isoleucine, leucine;
aspartic acid, glutamic acid;
asparagine, glutamine;
serine, threonine;
lysine, arginine;
phenylalanine, tyrosine.

Modifications (which do not normally alter primary sequence) include in vivo, or in vitro chemical derivatization of polypeptides, e.g., acetylation, or carboxylation. Also included are modifications of glycosylation, e.g., those made by modifying the glycosylation patterns of a polypeptide during its synthesis and processing or in further processing steps; e.g., by exposing the polypeptide to enzymes which affect glycosylation, e.g., mammalian glycosylating or deglycosylating enzymes. Also embraced are sequences which have phosphorylated amino acid residues, e.g., phosphotyrosine, phosphoserine, or phosphothreonine.

Also included are polypeptides or antibody fragments which have been modified using ordinary molecular biological techniques so as to improve their resistance to proteolytic degradation or to optimize solubility properties or to render them more suitable as a therapeutic agent. Analogs of such polypeptides include those containing residues other than naturally occurring L-amino acids, e.g., D-amino acids or non-naturally occurring synthetic amino acids. The peptides of the invention are not limited to products of any of the specific exemplary processes listed herein.

Substantially pure protein obtained as described herein may be purified by following known procedures for protein purification, wherein an immunological, enzymatic or other assay is used to monitor purification at each stage in the procedure. Protein purification methods are well known in the art, and are described, for example in Deutscher et al. (ed., 1990, *Guide to Protein Purification*, Harcourt Brace Jovanovich, San Diego).

The invention also includes a kit comprising the composition of the invention and an instructional material which describes administering the composition to a subject. In another embodiment, this kit comprises a (preferably sterile) solvent suitable for dissolving or suspending the composition of the invention prior to administering the composition.

As used herein, the term "physiologically acceptable" ester or salt means an ester or salt form of the active ingredient which is compatible with any other ingredients of the pharmaceutical composition, which is not deleterious to the subject to which the composition is to be administered.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

Although the descriptions of pharmaceutical compositions provided herein are principally directed to pharmaceutical compositions which are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, mammals including commercially relevant mammals such as cattle, pigs, horses, sheep, cats, and dogs, and to birds including commercially relevant birds such as chickens, ducks, geese, and turkeys.

Pharmaceutical compositions that are useful in the methods of the invention may be prepared, packaged, or sold in formulations suitable for oral, rectal, vaginal, parenteral, intravenous, topical, pulmonary, intranasal, buccal, ophthalmic, intrathecal or another route of administration. Other contemplated formulations include projected nanoparticles, liposomal preparations, resealed erythrocytes containing the active ingredient, and immunologically-based formulations.

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

In addition to the active ingredient, a pharmaceutical composition of the invention may further comprise one or more additional pharmaceutically active agents. Particularly contemplated additional agents include anti-emetics and scavengers such as cyanide and cyanate scavengers.

Controlled- or sustained-release formulations of a pharmaceutical composition of the invention may be made using conventional technology.

A formulation of a pharmaceutical composition of the invention suitable for oral administration may be prepared, packaged, or sold in the form of a discrete solid dose unit including, but not limited to, a tablet, a hard or soft capsule, a cachet, a troche, or a lozenge, each containing a predetermined amount of the active ingredient. Other formulations suitable for oral administration include, but are not limited to, a powdered or granular formulation, an aqueous or oily suspension, an aqueous or oily solution, or an emulsion.

As used herein, an "oily" liquid is one which comprises a carbon-containing liquid molecule and which exhibits a less polar character than water.

Liquid formulations of a pharmaceutical composition of the invention which are suitable for oral administration may be prepared, packaged, and sold either in liquid form or in the form of a dry product intended for reconstitution with water or another suitable vehicle prior to use.

Liquid suspensions may be prepared using conventional methods to achieve suspension of the active ingredient in an aqueous or oily vehicle. Aqueous vehicles include, for example, water and isotonic saline. Oily vehicles include, for example, almond oil, oily esters, ethyl alcohol, vegetable oils such as arachis, olive, sesame, or coconut oil, fractionated vegetable oils, and mineral oils such as liquid paraffin. Liquid suspensions may further comprise one or more additional ingredients including, but not limited to, suspending agents, dispersing or wetting agents, emulsifying agents, demulcents, preservatives, buffers, salts, flavorings, coloring agents, and sweetening agents. Oily suspensions may further comprise a thickening agent. Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, hydroxypropylmethylcellulose.

Known dispersing or wetting agents include, but are not limited to, naturally-occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g. polyoxyethylene stearate, heptadecaethyleneoxycetanol, polyoxyethylene sorbitol monooleate, and polyoxyethylene sorbitan monooleate, respectively). Known emulsifying agents include, but are not limited to, lecithin and acacia. Known preservatives include, but are not limited to, methyl, ethyl, or n-propyl-para-hydroxybenzoates, ascorbic acid, and sorbic acid. Known sweetening agents include, for example, glycerol, propylene glycol, sorbitol, sucrose, and saccharin. Known thickening agents for oily suspensions include, for example, beeswax, hard paraffin, and cetyl alcohol.

Liquid solutions of the active ingredient in aqueous or oily solvents may be prepared in substantially the same manner as liquid suspensions, the primary difference being that the active ingredient is dissolved, rather than suspended in the solvent. Liquid solutions of the pharmaceutical composition of the invention may comprise each of the components described with regard to liquid suspensions, it being understood that suspending agents will not necessarily aid dissolution of the active ingredient in the solvent. Aqueous solvents include, for example, water and isotonic saline. Oily solvents include, for example, almond oil, oily esters, ethyl alcohol, vegetable oils such as arachis, olive, sesame, or coconut oil, fractionated vegetable oils, and mineral oils such as liquid paraffin.

A pharmaceutical composition of the invention may also be prepared, packaged, or sold in the form of oil-in-water emulsion or a water-in-oil emulsion. The oily phase may be a vegetable oil such as olive or arachis oil, a mineral oil such as liquid paraffin, or a combination of these. Such compositions may further comprise one or more emulsifying agents such as naturally occurring gums such as gum acacia or gum tragacanth, naturally-occurring phosphatides such as soybean or lecithin phosphatide, esters or partial esters derived from combinations of fatty acids and hexitol anhydrides such as sorbitan monooleate, and condensation products of such partial esters with ethylene oxide such as polyoxyethylene sorbitan monooleate. These emulsions may also contain additional ingredients including, for example, sweetening or flavoring agents.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, intrasternal injection, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e. powder or granular) form for reconstitution with a suitable vehicle (e.g. sterile pyrogen-free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active ingredient in microcrystalline form, in a liposomal preparation, or as a component of a biodegradable polymer systems. Compositions for sustained release or implantation may comprise pharmaceutically acceptable polymeric or hydrophobic materials such as an emulsion, an ion exchange resin, a sparingly soluble polymer, or a sparingly soluble salt.

Formulations suitable for topical administration include, but are not limited to, liquid or semi-liquid preparations such as liniments, lotions, oil-in-water or water-in-oil emulsions such as creams, ointments or pastes, and solutions or suspensions. Topically-administrable formulations may, for example, comprise from about 1% to about 10% (w/w) active ingredient, although the concentration of the active ingredient may be as high as the solubility limit of the active ingredient in the solvent. Formulations for topical administration may further comprise one or more of the additional ingredients described herein.

A pharmaceutical composition of the invention may be prepared, packaged, or sold in a formulation suitable for ophthalmic administration. Such formulations may, for example, be in the form of eye drops including, for example, a 0.1-1.0% (w/w) solution or suspension of the active ingredient in an aqueous or oily liquid carrier. Such drops may further comprise buffering agents, salts, or one or more other of the additional ingredients described herein. Other opthalmically-administrable formulations which are useful include those which comprise the active ingredient in microcrystalline form or in a liposomal preparation.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the invention are known in the art and described, for example in Genaro, ed., 1985, *Remington's Pharmaceutical Sciences*, Mack Publishing Co., Easton, Pa., which is incorporated herein by reference.

Typically, dosages of the compound of the invention which may be administered to a subject, preferably a human, range in amount from 1 μg to about 100 g per kilogram of body weight of the subject. While the precise dosage administered will vary depending upon any number of factors, including but not limited to, the type of subject and type of disease state being treated, the age of the subject and the route of administration. Preferably, the dosage of the compound will vary from about 1 mg to about 10 g per kilogram of body weight of the subject. More preferably, the dosage will vary from about 10 mg to about 1 g per kilogram of body weight of the subject The compound may be administered to a subject as frequently as several times daily, or it may be administered less frequently, such as once a day, once a week, once every two weeks, once a month, or even lees frequently, such as once every several months or even once a year or less. The frequency of the dose will be readily apparent to the skilled artisan and will depend upon any number of factors, such as, but not limited to, the type and severity of the disease being treated, the type and age of the subject, etc.

The invention also includes a kit comprising the composition of the invention and an instructional material which describes adventitially administering the composition to a cell or a tissue of a subject. In another embodiment, this kit comprises a (preferably sterile) solvent suitable for dissolving or suspending the composition of the invention prior to administering the compound to the subject.

As used herein, an "instructional material" includes a publication, a recording, a diagram, or any other medium of expression which can be used to communicate the usefulness of the peptide of the invention in the kit for effecting alleviation of the various diseases or disorders recited herein. Optionally, or alternately, the instructional material may describe one or more methods of alleviation the diseases or disorders in a cell or a tissue of a subject. The instructional material of the kit of the invention may, for example, be affixed to a container which contains the peptide of the invention or be shipped together with a container which contains the peptide. Alternatively, the instructional material may be shipped separately from the container with the intention that the instructional material and the compound be used cooperatively by the recipient.

Example I

Methods

Cell Culture, Plasmid Constructs and Transfection

The human salivary gland ductal (HSG) cell line was provided by Matthew Hoffman (NIDCR, Bethesda Md.). HSG cells were cultured in DMEM/F12 with 10% FBS. Cells were assayed between passage 10 and 20. Some HSG cells were transfected with a SMARTpool of four human SDC1 (Ambion Inc, Austin Tex.) or heparanase-1 or heparanase-2 specific siRNAs at different doses (Dharmacon Inc, Lafayette Colo.). Other cells were transfected with individual siRNAs also at different doses. siRNAs sequences are as follows: (i) SDC1 siRNAs, CGACAAUAAACGGUACUUGTT (SEQ ID NO: 2), GGAGGAAUUCUAUGCCUGA (SEQ ID NO: 3), GGACUUCACCUUUGAAACCTT (SEQ ID NO: 5), and GGUAAGUUAAGUAAGUUGATT (SEQ ID NO: 6) (gene bank accession no: NM_002997); SDC2 siRNAs, GGAGUUUUAUGCGUAAAACTT (SEQ ID NO: 7), GGAUGUAGAGAGUCCAGAGTT (SEQ ID NO: 8), and GGAGUGUAUCCUAUUGAUGTT (SEQ ID NO: 9) (gene bank accession no: NM_002998); heparanase-1 siRNAs, GCAAUGAACCUAACAGUUUUU (SEQ ID NO: 10), GAUCAAACCUUGCCACCUUUU (SEQ ID NO: 11), GGACUGGACUUGAUCUUUGUU (SEQ ID NO: 14), and GAACAGCACCUACUCAAGAUU (SEQ ID NO: 15) (gene bank accession no: NM_006665). Heparanase-2 siRNA sequences from Dharmacon were not made publicly available. Also utilized was Ambion's negative control siRNA #1 (catalogue no. 4611). Silencing efficiency was evaluated by protein blotting and RT-PCR. HEK293T cells were purchased from and propagated as suggested by ATCC (Manassas Va.). HEK293T cells were transfected with a Bgl II linearized expression vector coding for human SDC1 (hS1-pcDNA3) using Lipofectamine™ 2000 reagent (Invitrogen Life Technologies, Carlsbad Calif.). Stable populations expressing SDC1 were selected in culture medium containing 400 ng/ml G418. A human SDC1 deletion construct lacking 51 amino acids from the N-terminus ('del 1-51') was generated from hS1-pcDNA3 by long range reverse PCR using forward primer 5'-GGTGGTGGATCCACGCAGCTCCT-GACGGCTATTCCC-3' (SEQ ID NO: 16) and reverse primer 5'-GGTGGTGGATCCCAGGCTCAGCGC-CAGCGCGCACAG-3' (SEQ ID NO: 17) containing BamH1 sites. Amplicons were cut using BamH1, ligated as plasmid. Human SDC 1 'del 51-252' (only N-terminal 50 amino acids of ectodomain linked to the transmembrane and cytoplasmic domains) was similarly generated from hS1-pcDNA3 using forward primer 5'-CTAGCTAGCTTGCAAAGCACCTG-CACCTG-3' (SEQ ID NO: 18) and reverse primer 5'-CTAGCTAGCGAGGTG CTGGGAGGGGTC-3' (SEQ ID NO: 19). This introduced NheI sites 5' of the codon for Ala51 and 3' of the codon for Glu252 (most C-terminal ectodomain amino acid). Amplicons were digested with NheI and ligated as plasmid. Human SDC1 'del 51-310' (only N-terminal 50 amino acids of ectodomain) N-50 amino acids only was PCR amplified from hS1-pcDNA3 using forward primer 5'-CTATAGGGAGACCCAAGCTTGGTACCGAG-3' (SEQ ID NO: 20) and reverse primer 5'-CCGGAATTCAG- CACCTGCACCTGAG-3' (SEQ ID NO: 21) containing HindIII and EcoR1 sites. Amplicons were digested with HindIII and EcoR1 to create cohesive ends, subsequently purified and ligated into the HindIII/EcoR1 site of the pcDNA vector. All constructs were confirmed by DNA sequencing. Plasmids were transfected into HEK293T cells, and stable or transient transfectants generated. Generation of HEK293T cells stably transfected with human SDC2 or SDC4 was previously described (Utani et al., 2001). Development of lacritin-intein constructs and purification are described elsewhere (Wang et al., submitted). A lacritin-GST construct was prepared by subcloning lacritin cDNA into pGEX4T-2 (Amersham Biosciences, Piscataway N.J.) using Sap1 and NdeI, in-frame with GST. Recombinant plasmids were transformed into *E. coli* strain BL21. Bacterial cultures were expanded and fusion protein purified on Glutathione-Sepharose 4B (Amersham Biosciences, Piscataway N.J.). A human SDC1 ectodomain-GST construct was generated from pGEX-2T hS1ED and similarly purified.

Lacritin Affinity Chromatography

Cell surface biotinylation, and affinity chromatography followed the method of Chen et al (1997). Briefly, six 150 mm culture dishes of 80% confluent HSG cells were washed twice on ice with ice-cold PBS and incubated for 30 min with EZ-Link Sulfo-NHS-LC Biotin (Pierce, Rockford Ill.). Cells were then washed twice with PBS-glycine, gently loosened with a cell scraper, and pelleted at 4° C. The pellet was twice resuspended in 25 ml PBS-glycine, and incubated for 30 min in 1 ml lysis buffer (50 mM Tris HCl, pH 7.4, 100 mM NaCl, 5 mM MnCl2, 2 mM PMSF, 200 mM n-octyl-β-D-glucopyranoside, and protease inhibitors (Roche Diagnostics, Penzberg Germany)). Lysate was centrifuged for 15 min at 4° C., and the supernatant applied to a 1 ml pre-column then washed through with 1 ml of binding buffer (50 mM Tris HCl, pH 7.4, 100 mM NaCl, 5 mM MnCl2, 2 mM PMSF, 50 mM n-octyl-β-D-glucopyranoside) and collected. Half was applied to a lacritin-intein column in which lacritin was coupled to chitin beads via chitin-binding intein, and the other half to a negative control column that included an approximately equivalent molar amount of intein-chitin only. Columns were rotated end-to-end overnight at 4° C., then each was washed with 20 column volumes of affinity column buffer and eluted with the same buffer containing 1 M NaCl. Twenty 100 µL fractions were collected per column. Fractions were run on 8% SDS-PAGE gels, and silver stained or transferred to nitrocellulose for blotting with streptavidin peroxidase. For the latter, blots were blocked with PBS containing 0.1% Tween-20 and 2.5% milk for 1 h at 37° C., washed three times with PBS/0.1% Tween-20, incubated in 50 ml of 1:1000 streptavidin-horseradish peroxidase conjugate (Amersham Biosciences, Piscataway N.J.) in PBS/0.1% Tween-20, washed five times with the same buffer and then detected using ECL reagent (Pierce, Rockford Ill.). Bands of interest were excised and sequenced by mass spectroscopy (Biomolecular Research Facility, University of Virginia).

Affinity Precipitation Binding

Human SDC1, SDC2, or SDC4 stably-expressing HEK293T cells were harvested on ice into 1 ml of the same lysis buffer used for affinity chromatography. Lysates were cleared by centrifugation (20,000×g) at 4° C., and protein concentration of supernatant was estimated by the BCA assay (Pierce, Rockford Ill.). Lacritin-intein or lacritin-GST (5 µg) and FGF2-GST fusion proteins were respectively bound to chitin beads (New England Biolabs, Ipswich Mass.) or glutathione-Sepharose beads (Amersham Biosciences, Piscataway N.J.). Beads were incubated with lysates (~200 µg of SDC1 stably expressing HEK293T cells) overnight at 4° C., and washed three times with binding buffer as above (each wash three times the bead volume). In competition assays, SDC1 lysates were mixed with increasing amounts of soluble lacritin, HS, HS plus CS (Seikagaku America, Falmouth Mass.), bacterially expressed human SDC1 ectodomain (hS1ED), native SDC2, native SDC4, N-24 or C-25. Mixtures were then applied to lacritin immobilized beads, and further studied as described below. For sequential pull down assays, cell lysates were sequentially affinity precipitated with FGF2-GST or lacritin-intein. After FGF2-GST depletion of all available FGF-bindable SDC1, one-half was precipitated with lacritin-intein. The other half was methanol precipitated overnight and resuspended in heparitinase buffer. Similarly, after lacritin-intein depletion of all available lacritin-bindable SDC1, one-half was precipitated with FGF2-GST and the other half precipitated by methanol overnight, then resuspended in heparitinase buffer. The reactions were separated by SDS-PAGE, and blotted using anti-SDC1 mAb B-B4 (Serotec, Oxford UK) or anti-SDC2 polyclonal antibody L-18 or anti-SDC4 polyclonal antibody N-19 (Santa Cruz Biotechnology, Santa Cruz Calif.) followed by ECL detection (Pierce, Rockford Ill.).

For SDS-PAGE and immunoblotting, beads were digested with heparitinase I (Seikagaku America, Falmouth Mass.) and chondroitin ABC lyase (MP Biochemicals, Aurora Ohio) since native syndecans migrate as a heterodisperse smear in SDS-PAGE. Briefly, beads were resuspended in heparitinase buffer (50 mM Hepes, pH 6.5, 50 mM NaOAc, 150 mM NaCl, 5 mM CaCl2) with 0.0001 units heparitinase and 0.005 units chondroitin ABC lyase for 2 h at 37° C. A second aliquot of each enzymes was added for an additional 2 h. Samples were diluted with 2× sample buffer, separated by 10% SDS-PAGE, transferred to Immobilon-P PVDF (Millipore, Billerica, Mass.) for 4 h at 300 mA, fixed for 30 min in PBS containing 0.05% glutaraldehyde (Sigma, Saint Louis Mo.), and blocked overnight at 4° C. in TBS (10 mM Tris, 150 mM NaCl, pH 7.4) with 3% BSA. mAb B-B4 diluted in blocking buffer was incubated with blots for 2 h at RT, washed five times with 10 mM Tris, 150 mM NaCl, pH 7.4 containing 0.1% Tween-20 and detected with alkaline-phosphatase conjugated secondary antibody (Amersham Biosciences, Piscataway N.J.) using ECL.

Heparanase Detection

For analysis, cellular heparanase was enriched by HiTrap heparin affinity purification (Amersham Biosciences, Piscataway N.J.). Briefly, HSG or HEK293 lysates were dialyzed overnight against binding buffer (10 mM sodium phosphate, pH 7) and applied to the column. After washing with 10 column volumes of binding buffer, heparanase was eluted using 5 column volumes of elution buffer (10 mM sodium phosphate, 2 M NaCl, pH 7). Protein concentration was determined by BCA and analyzed by 10% SDS-PAGE. Heparanase-1 was detected with rabbit polyclonal antibodies directed against human heparanase (kindly provided by Israel Vlodaysky, Rappaport Faculty of Medicine, Haifa, Israel) followed by HRP-conjugated secondary antibody and ECL.

Mitogenesis Assay

HSG cells in serum-containing media were seeded in 24-well plates at a density of 0.5×105 cells/well. After 24 h, the medium was changed to Minimum Essential Medium Alpha Modification with washes for 24 h, then lacritin was added for 24 h to a final concentration of 10 nM in the same medium containing [3H]-thymidine (2 µCi/ml). Cells were incubated alone with lacritin or together with increasing amount of bacterial-expressed human SDC1 ectodomain (hS1ED) as a soluble inhibitor. Cells depleted of heparanase-1 or SDC1 were treated with lacritin in [3H]-thymidine 48 h after siRNA transfection. To rescue heparanase depleted cells, ~1 µg heparanase enriched from HSG or HEK293 cells using heparin affinity column or 0.0001 units bacterial heparitinase (Seikagaku America) was added together with lacritin and [3H]-thymidine for 24 h. [3H]-thymidine incorporation was stopped by placing on ice. Cultures were washed twice with ice-cold PBS, fixed with cold and then RT TCA (10%) for 10 min each, washed twice with RT PBS, collected in 1 N NaOH, neutralized with 1 N HCl, and then transferred to liquid scintillation vials for measurement.

HS Chain Analysis

50% confluent HSG cell cultures in 150-mm culture dishes were metabolically labeled with 50 µCi/ml Na2 35SO4 (1494 Ci/mmol; PerkinElmer, Boston Mass.) in DMEM for 48 h as described by Zako et al. (2003). Both normal and heparanase-1 depleted cells were labeled. After washing three times with PBS, cell lysates were collected and affinity precipitated with FGF2-GST or lacritin-intein overnight at 4° C. SDC1 bound to beads was digested with chondroitin ABC lyase (MP Biochemicals, Aurora Ohio) for 3 h at 37° C., eluted with 2 M NaCl and then subjected to eliminative cleavage and reduction of HS by adjusting to 100 mM NaOH/1 M NaBH4 for 24 h at 37° C. Released HS was neutralized by drop wise addition of 1M HCl and subjected to Sepharose CL-6B column (1×57 cm) gel filtration chromatography in PBS at a flow rate 16 ml/h. Radioactivity was measured by liquid scintillation counting. The void volume (V0, fraction 26) and total column volume (Vt, fraction 62) were respectively determined using dextran blue and sodium dichromate as markers.

Other Methods—Other methods useful in the present invention are described in PCT Publication PCT/US0225/016112 (WO 2005/119899) and in U.S. patent application Ser. No. 10/468,372.

Results:

Lacritin Targets Cell Surface SDC1

Figure 1B:
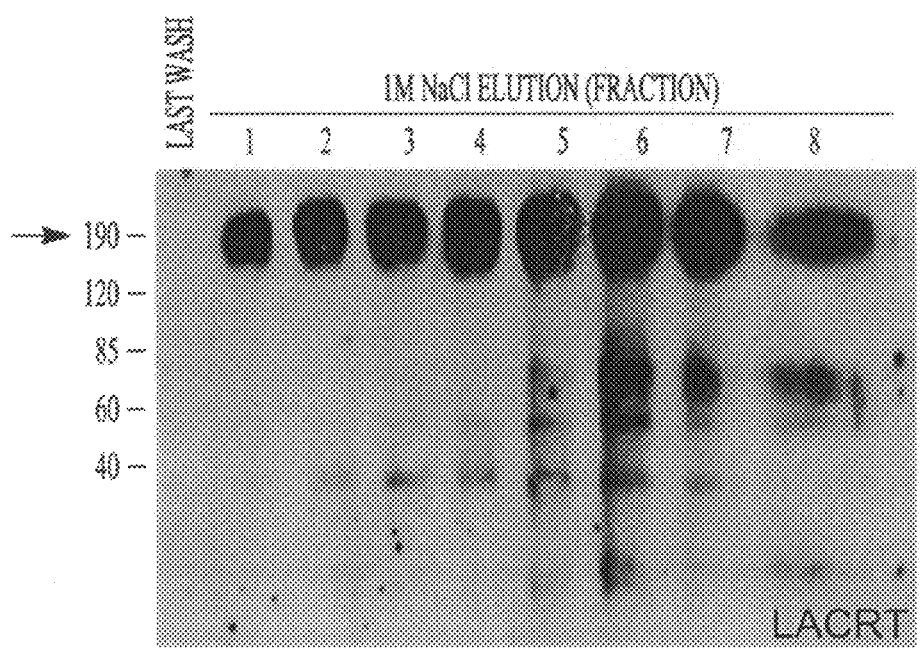

Lacritin promotes epithelial proliferation at low nanomolar levels, suggesting a cell surface binding $K_d$ in the nanomolar range sufficient for affinity purification of its receptor. An apparent 190 kDa cell surface protein eluted from lacritin, but not control, columns after incubation with detergent lysates of surface biotinylated human salivary ductal (HSG) cells in buffer containing physiological levels of salt (FIG. 1). Sequencing identified the 190 kDa protein as a multimer of human SDC1, a transmembrane proteoglycan that acts as a co-receptor for mitogenic signaling by binding heparin-binding growth factors such as FGFs, HGFs, Wnts, Hhs, and HGFs via its HS glycosaminoglycan chains (Alexander et al., 2000; Esko and Selleck, 2002).

Figure 2A:
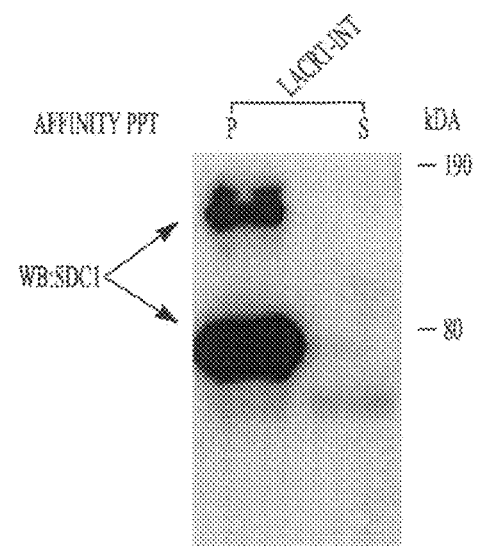
FIG. 2. Lacritin binding to SDC1 is independent of complete HS/CS glycosaminoglycans. (A) Lacritin affinity precipitation of human SDC1 multimers stably expressed by HEK293T cells. Lacritin-intein beads were incubated with cell lysates, washed extensively, and treated with heparitinase I/chondroitinase ABC. Pellet (P) and supernatant (S) from the centrifuged digest were then blotted with mAb B-B4 for SDC1 core protein. (B) Lacritin-intein, lacritin-GST, FGF2-GST, intein and GST beads were incubated with lysates from the same HEK293T cells stably expressing human SDC1. Precipitates were washed, treated, centrifuged and blotted identically as above. (C) Lacritin-intein and FGF2-GST beads were incubated with lysate of HEK293T cells stably expressing human SDC2 or lysate of another HEK293T cell line stably expressing human SDC4. Beads were washed, treated and centrifuged identically as above. Blots were detected with anti-SDC2 mAb L-18 or anti-SDC4 mAb N-19 respectively. (A) shows both 190 and 80 kDa bands. (B) and (C), and all subsequent figures show the 80 kDa band which is more predominant in HEK293T transfectants.
Figure 2B:
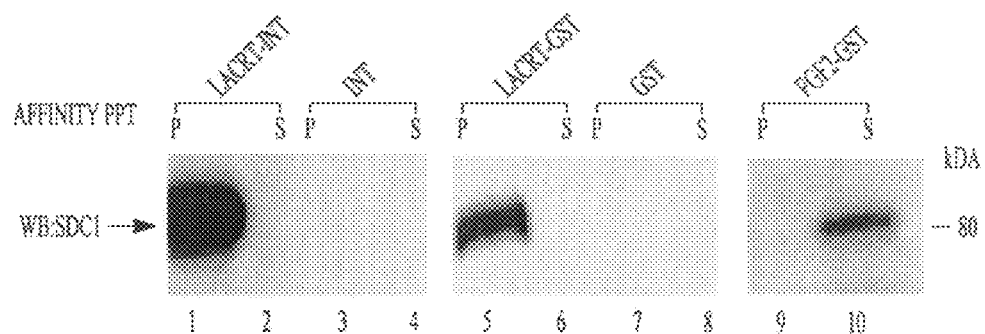
Figure 2C:
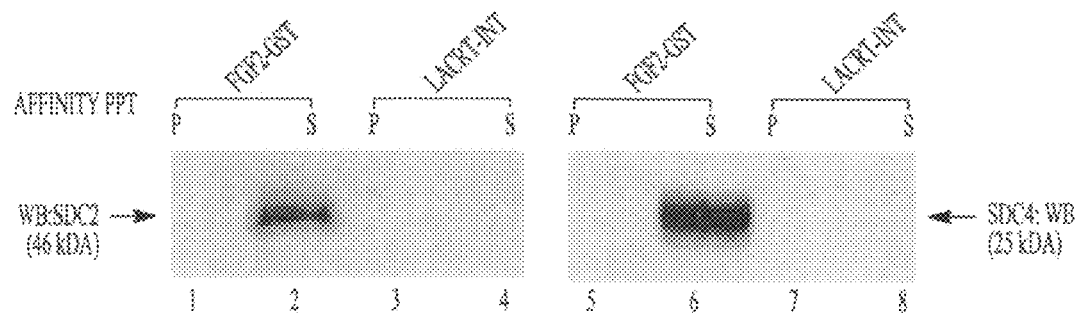

To assess this interaction by affinity precipitation, we created a 293T cell line stably expressing human SDC1, and treated lacritin or positive control FGF2 precipitates with bacterial heparitinase and chondroitinase to remove the large and heterogenous glycosaminoglycan chains. The supernatant and pellet of the digest were then separately blotted for SDC1 using mAb B-B4 directed against the core protein. This revealed 190 and 80 kDa bands, confirming the multimeric nature of the 190 kDa SDC1 band (FIG. 2A). Lacritin-bound SDC1 was consistently detected in the pellet, implying that the ligation was not solubilized by heparitinase/chondroitinase digestion and therefore may involve the core protein. In keeping with this possibility, lacritin did not target SDC2 or SDC4 (FIG. 2C) that share HS chains but only 27-28% ectodomain identity with SDC1. FGF2 as expected bound all three syndecans via heparitinase cleavable HS (FIG. 2B, C).

SDC1 Binding Via a Lacritin C-Terminal Domain

Figure 3A:
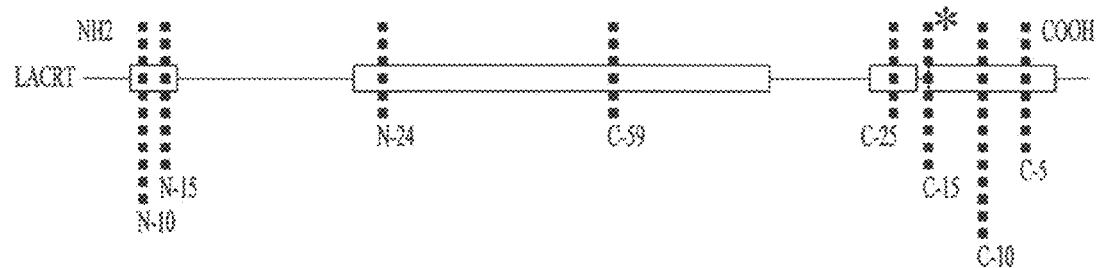
FIG. 3. Lacritin's C-terminus binds SDC1. (A) Schematic diagram of lacritin with dotted lines indicating N- and C-terminal truncations. All lacritin truncations were expressed as intein fusion proteins for affinity precipitation. Asterisk indicates mitogenic domain (Wang et al, submitted), and boxes represent PSIPRED-predicted alpha helices. (B) Lacritin-, C-5-, C-10-, C-15-, C-25- and C-59-intein beads were incubated with lysates from HEK293T cells stably expressing human SDC1. Beads were washed and treated with heparitinase I/chondroitinase ABC. The digests were centrifuged, and pellets (P) and supernatants (S) blotted with mAb B-B4 for SDC1 core protein, all as in FIG. 2. (C) Incubation of lacritin-, N-15- and N-24-intein beads with the same human SDC1 lysates was followed with identical washing, heparitinase I/chondroitinase ABC digestion, centrifugation and B-B4 mAb blotting. Lys, lysate.
Figure 3B:
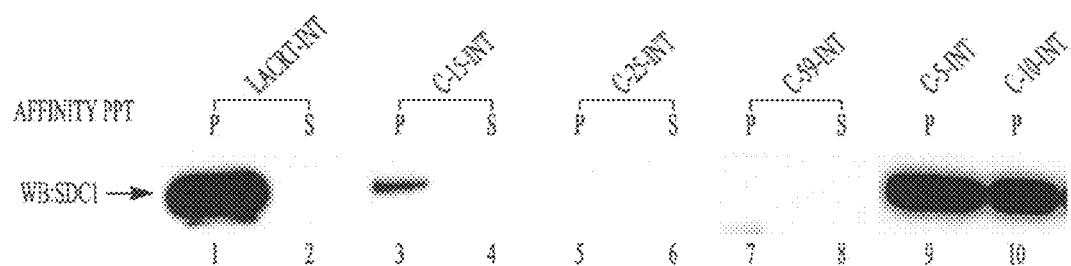
Figure 3C:
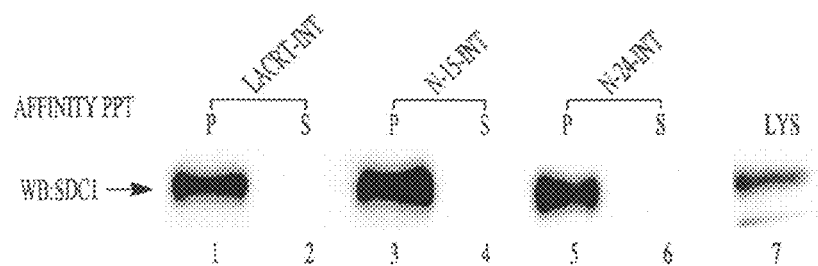
Figure 4A:
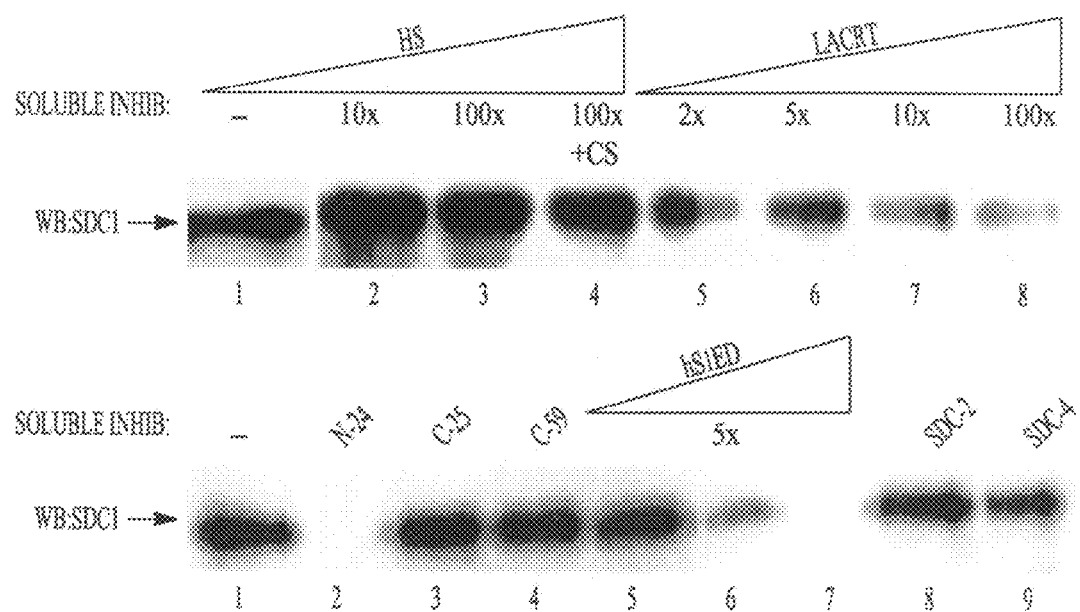
FIG. 4. Lacritin-SDC1 binding is inhibited by soluble hS1ED, lacritin and N-24, but not by C-25, C-59, HS, CS, SDC2 or SDC4. (A) Top row, lacritin-intein beads were incubated with human SDC1 lysates from stably expressing HEK293T cells in the presence of increasing amounts of soluble HS (70-700 µg), HS (700 µg) plus CS (700 µg), lacritin (14-700 µg) or no inhibitor (−). Quantity of soluble inhibitor was calibrated relative to the approximately 7-8 µg of human SDC1 elutable from lacritin-intein beads with 1 M NaCl. After incubation, beads were washed extensively and treated with heparitinase I/chondroitinase ABC. The digests were centrifuged, and pellets blotted with mAb B-B4 for SDC1 core protein, as in FIG. 2. Bottom row, lacritin-intein beads were incubated with human SDC1 lysates in the presence of soluble N-24, C-25, C-59 (14 µg of each), increasing amounts of bacterially expressed human SDC1 ectodomain (hS1ED; 35-700 µg), or with HEK293T cell-expressed native SDC2 or native SDC4 (70 µg of each). Beads were washed and treated identically as above. (B) Quantification of inhibition binding.
Figure 4B:
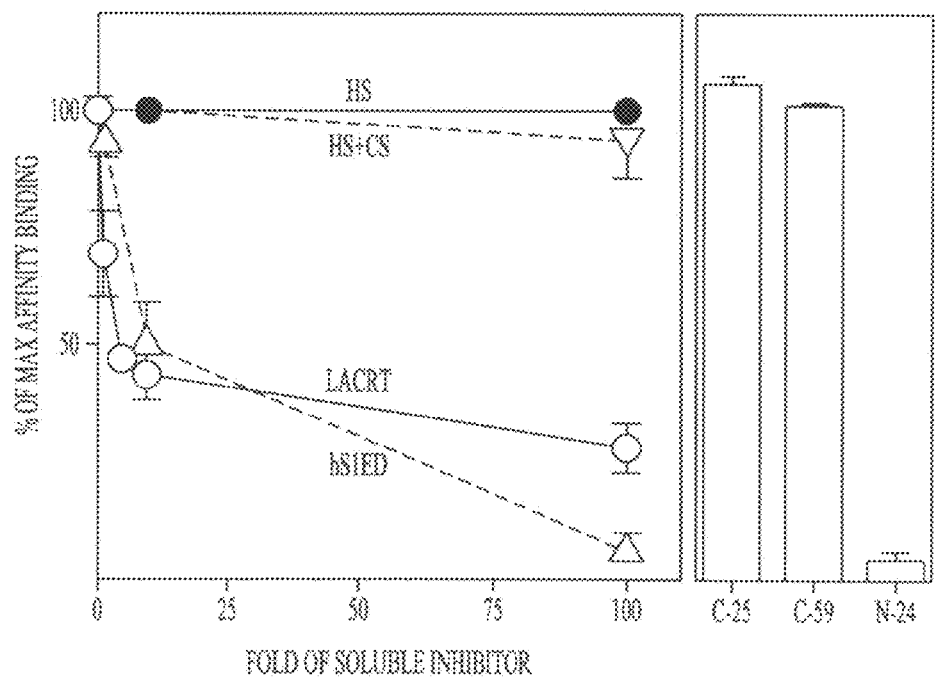

Lacritin truncation analysis recently identified a C-terminal mitogenic domain capable of forming an amphipathic alpha helix as per the receptor binding domain of PTHLP (Wang et al., 2006). Could SDC1 binding and mitogenic sites be shared? SDC1 binding was unaffected by deletion (FIG. 3A) of five and ten amino acids from the C-terminus (FIG. 3B), or fifteen and twenty-four amino acids from the N-terminus (FIG. 3C) of lacritin. However, affinity was substantially diminished after five more C-terminal amino acids were deleted (C-15) and completely abolished from C-25 and C-49 lacritin (FIG. 3B). These data point to a binding site between amino acids 100 and 109 of mature lacritin that mirrors the mitogenic domain. To validate and further probe this observation, lacritin-SDC1 affinity precipitations were competitively challenged with the truncated lacritin mutants (FIG. 4). Soluble lacritin and N-24, but not C-25 and C-59 inhibited binding. Also inhibitory was recombinant human SDC1 core protein (hS1ED) expressed in E. coli, but not HS, CS nor human SDC2 or SDC4. Taken together, these data suggest that ligation of SDC1 is specified by a region within lacritin's C-terminus that appears to show affinity for SDC1's core protein but not HS or CS.

SDC1 is Required for Lacritin Mitogenesis

Figure 5A:
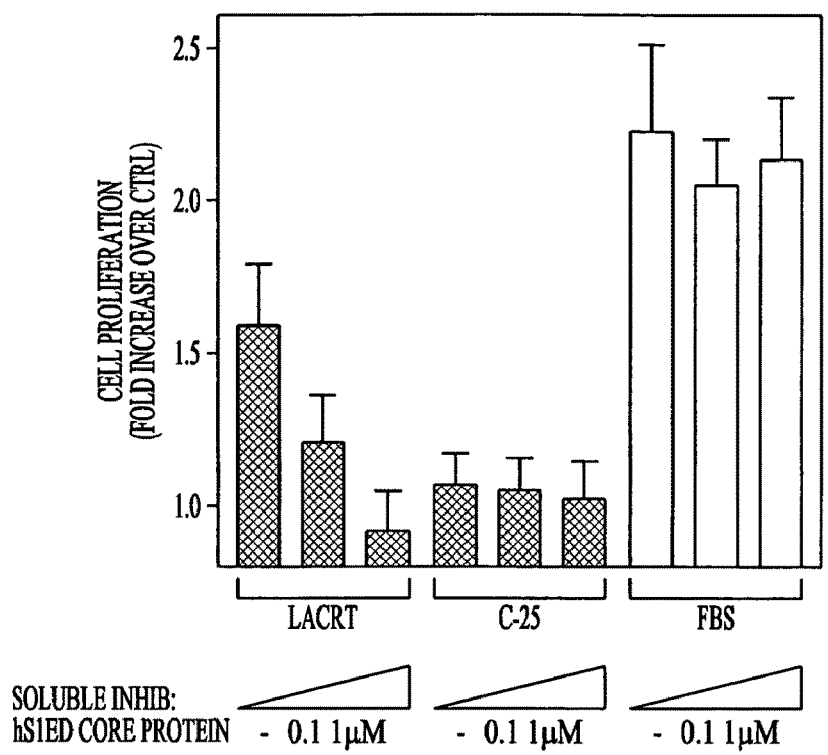
FIG. 5. SDC1 is required for lacritin-dependent mitogenesis and COX2 expression. (A) Proliferation assay in which HSG cells were grown for 24 h in serum-free media containing 10 nM lacritin, 10 nM C-25 lacritin or FBS in the absence or presence of increasing amounts of soluble hS1ED. (B) Identically performed proliferation assay in which HSG cells were treated with 10 nM lacritin or FBS 48 h after being mock transfected, or transfected with 10 nM of Ambion's negative control siRNA #1 (neg), 1-100 nM SDC1 siRNA, or 10 nM SDC2 siRNA. (C) Above, RT-PCR and Western blotting of mock vs SDC1 siRNA (10 nM)-treated cells. RT-PCR is for SDC1 and SDC2 mRNAs. Blotting is with mAb B-B4 for SDC1 core protein, or with anti-GAPDH. Below, RT-PCR for SDC2 mRNA in mock transfected cells or cells transfected with 10 nM SCD2 siRNA. (D) RT-PCR of COX2 expression by HSG cells without (−) or with (+) 10 nM lacritin stimulation. 48 h earlier the cells were mock transfected or transfected with 10 nM SDC1, 10 nM SDC2 or 1 nM heparanase-1 (HPSE-1) siRNAs. At bottom is GAPDH expression.
Figure 5B:
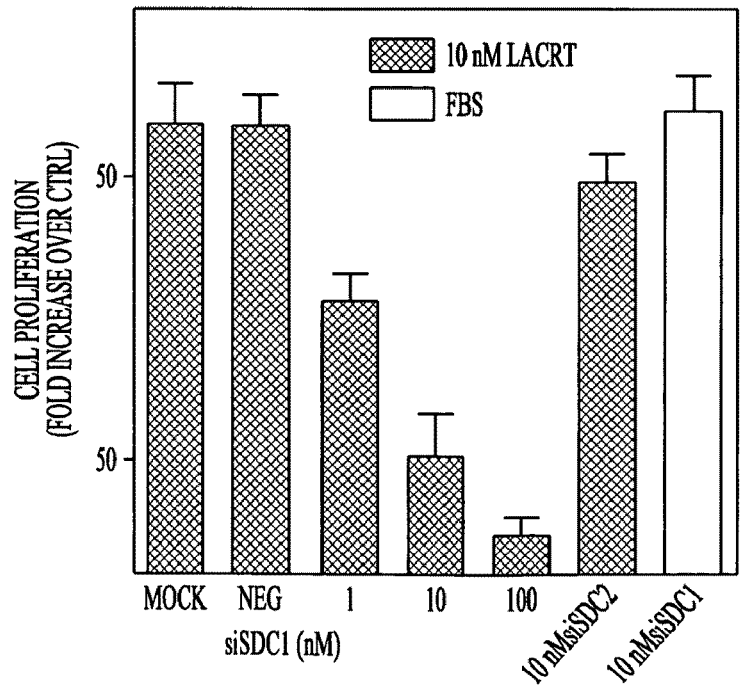
Figure 5C:
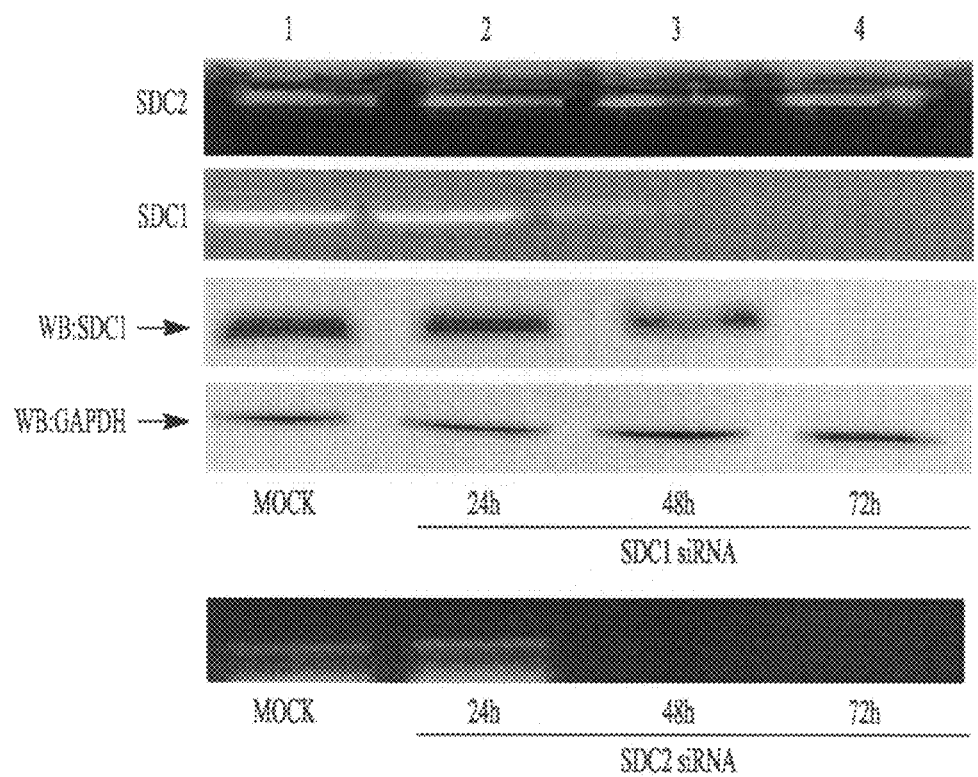
Figure 5D:
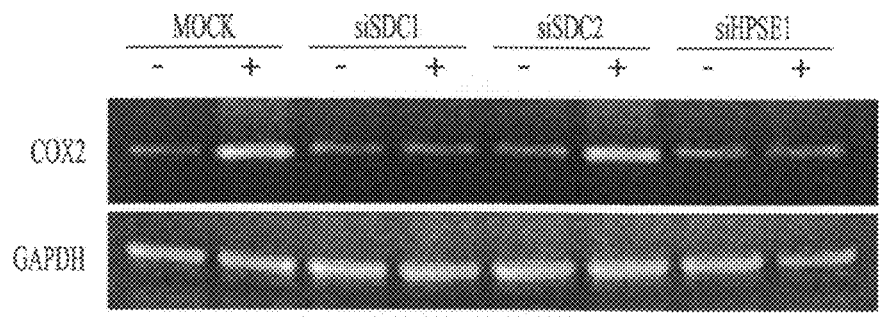

Since mitogenic (Wang et al, submitted) and SDC1 binding domains map to the same ten amino acid region, we questioned whether competition with recombinant hS1ED would disrupt lacritin-dependent mitogenesis. Soluble hS1ED inhibited proliferation of lacritin-stimulated HSG cells in a dose-dependent manner. The same inhibitory doses had no effect on C-25 treated cells nor on FBS stimulated proliferation (FIG. 5A). To approach this question differently, HSG cells were depleted of SDC1 by siRNA (FIG. 5C). Dose-dependent depletion of SDC1, but not depletion of SDC2 (FIG. 5C), completely abrogated lacritin mitogenic responsiveness (FIG. 5B). Lacritin signals through Gαi or Gαo/PKCα-PLC/Ca2+/calineurin/NFATC1/COX-2 toward mitogenesis (Wang et al, submitted). We therefore examined COX-2 expression in SDC1 and SDC2 depleted cells. In SDC1, but not SDC2, knockdown cells lacritin-dependent COX-2 expression was absent (FIG. 5D). Ligation of SDC1 thus appears to be a required upstream step in lacritin mitogenic signaling.

Lacritin and FGF2 Target Different Forms of SDC1

Figure 6A:
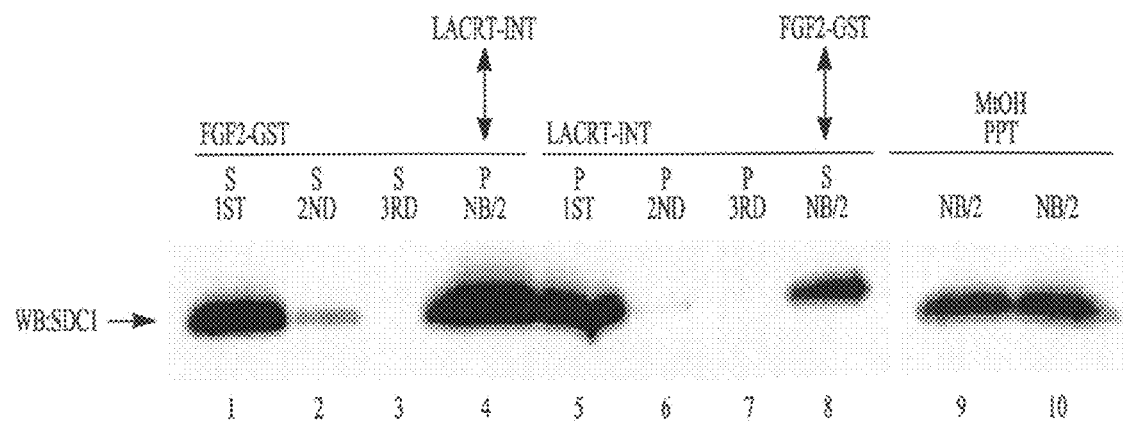
FIG. 6. Lacritin and FGF2 bind different forms of cell surface SDC1. (A) Sequential affinity precipitation assays. Lanes 1-3, lysate from human SDC1 stably expressing HEK293T cells was sequentially incubated with three rounds of fresh FGF2-GST beads. Half of the final depleted lysate was then incubated with lacritin-intein beads (lane 4) and the other half was methanol precipitated (lane 9). Similarly in lanes 5-7, a different aliquot of lysate from the same cells was sequentially incubated with three rounds of fresh lacritin-intein beads. Half of the final depleted lysate was then incubated with FGF2-GST beads (lane 8) and the other half was methanol precipitated (lane 10). Beads were washed and treated with heparitinase I/chondroitinase ABC. The digests were centrifuged, and pellets (P) and supernatants (S) blotted with mAb B-B4 for SDC1 core protein. Respectively shown are digest supernatants (lanes 1-3 and 8) and pellets (lanes 4-7) as per heparitinase release of FGF2-bound or resistance of lacritin-bound SDC1. (B) HEK293T cells stably expressing human SDC1 were either lysed as usual, or first briefly trypsinized (<5 min; 0.05%) then treated with serum to inactivate trypsin, washed and lysed. Both lysates were incubated with lacritin-intein beads. Beads were washed, treated with heparitinase I/chondroitinase ABC. The digests were centrifuged, and pellets (P) and supernatants (S) blotted with mAb B-B4 for SDC1 core protein. (C) Lysates from HEK293T cells stably expressing human SDC1 were incubated with lacritin-intein beads. Beads were washed and either left untreated (lane 1) or treated with heparitinase I/chondroitinase ABC (lanes 2, 3). The treated sample was centrifuged. Pellet (P; lane 2), supernatant (S; lane 3), untreated precipitate (lane 1), starting lysate (lane 4) and lacritin-intein solubilized from fresh lacritin-intein beads were blotted with mAb 3G10 for desaturated uronates in SDC1.
Figure 6B:
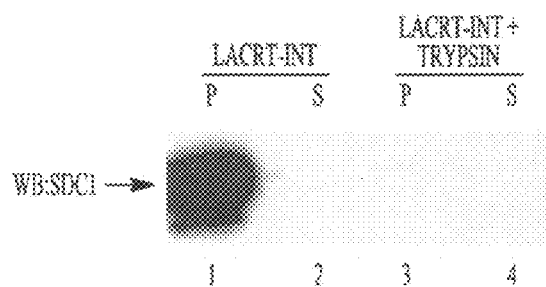
Figure 10:
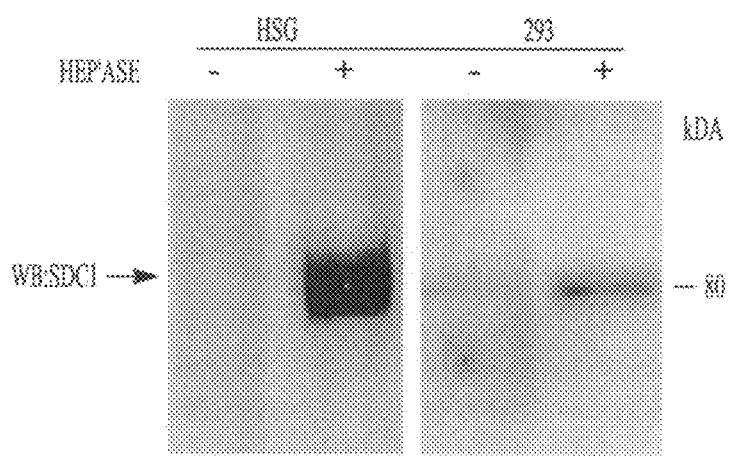
FIG. 10. Size heterogeneity of native SDC1 is attributable to its HS and CS chains. Lysates of HSG and HEK293T cells stably expressing human SDC1 either without (−) or with (+) heparitinase I/chondroitinase ABC digestion. Blotting is with mAb B-B4 for SDC1 core protein.
Figure 11:
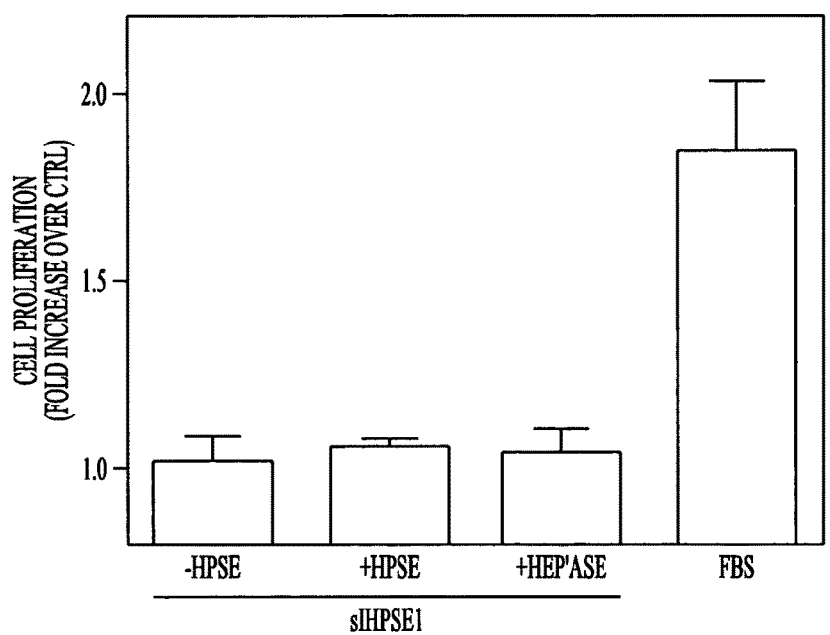
FIG. 11. Heparanase and heparitinase alone are not mitogenic for HSG cells. Mitogenic assay in which HPSE1-depleted HSG cells were incubated for 24 h with 1 µg of heparanase (enriched fraction from HEK293T) or with 0.0001 U of bacterial heparitinase in the presence of 3H-thymidine. FBS serves as a positive control.

We noted how biotinylated SDC1 from surface-labeled HSG cells was selectively purified on lacritin affinity columns and that it migrated as a relatively distinct band (FIG. 1) without prior heparitinase/chondroitinase to excise the heterogenous HS and CS chains. In contrast, native SDC1 without digestion presents as a broad smear (FIG. 10). Also, lacritin affinity precipitated SDC1 was retained in the pellet after heparitinase/chondroitinase digestion. Could the sharply defined 190 and 80 kDa bands represent a minor deglycanated or hypoglycosylated form preferentially enriched because of lacritin's apparent core protein-related affinity? To explore this possibility, we sequentially depleted either FGF2- or lacritin-bindable SDC1 from lysates then challenged the depleted lysates respectively with lacritin or FGF2 affinity precipitation (FIG. 6). Affinity precipitates were treated with heparitinase/chondroitinase prior to SDS-PAGE to simplify mAb B-B4 detection of the core protein in the digest supernatant (FGF2) or pellet (lacritin). Successive pull-down with FGF2-GST depleted all FGF2-bindable SDC1 (FIG. 6A, lanes 1-3). Interestingly, the amount of SDC1 available to interact with lacritin-intein was unaffected (FIG. 6A, lane 4 versus lanes 1 and 9). Similarly, depletion of SDC1 with lacritin-intein slightly but not substantially diminished SDC1 binding to FGF2-GST (FIG. 6A, lanes 5-7 versus lanes 8 and 10). This implies that two pools of SDC1 may be available. One is apparently native SDC1, to which lacritin appears to lack affinity. The other may be an HS-free or partially deglycanated form of SDC1. Could the latter be an immature intracellular form? This appears not to be the case. When cells were gently trypsinized prior to lysis, no lacritin-bindable SDC1 was detected (FIG. 6B) in keeping with the original purification of labeled SDC1 from surface biotinylated cells (FIG. 1). Also ruled out was bacterial heparitinase contamination of recombinant lacritin.

Figure 6C:
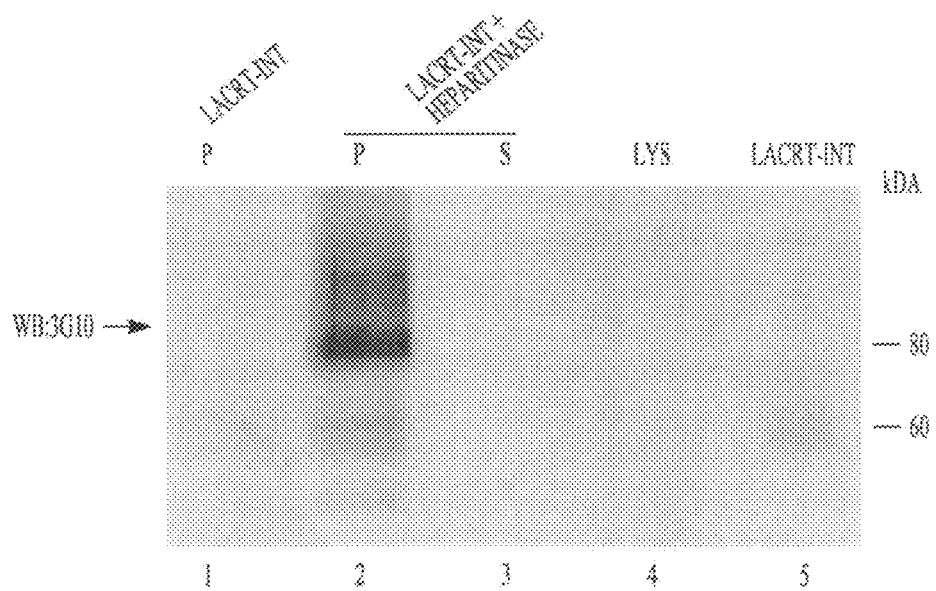

We took advantage of 3G10 mAb directed against a desaturated uronate epitope generated by heparitinase digestion (David et al., 1992) and could detect lacritin-bound SDC1 only after treatment with exogenous heparitinase (FIG. 6C). That heparitinase can create the 3G10 epitope is revealing, for it points to the presence of HS or HS stubs on the core protein that is recognized by lacritin. HS stubs could be generated by heparanase, a eukaryotic endo-β-D-glucuronidase that cleaves the entire HS chains between GlcUA and GlcNAc linkages. Taken together these data suggest that lacritin and FGF2 target different forms of cell surface SDC1. SDC1 bound by lacritin is less heterogenous, suggesting that although it is decorated with sufficient HS to be recognized by heparitinase, much of its HS has been removed.

Heparanase-Dependent Lacritin Mitogenesis

Figure 7A:
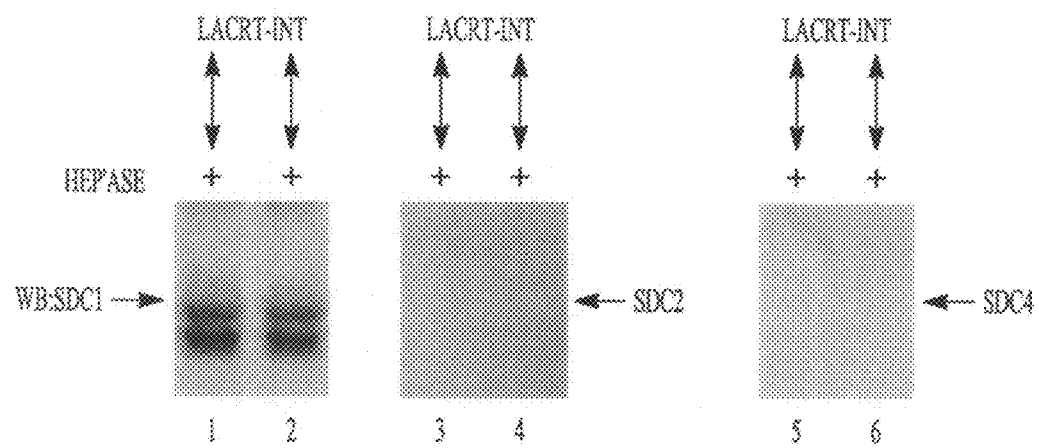
FIG. 7. Bacterial heparitinase digestion exposes FGF2-bindable SDC1 to lacritin-binding via a domain in SDC1's N-terminal 50 amino acids. (A) Human SDC1, SDC2 and SDC4 from stably expressing HEK293T cells were individually purified on FGF2-GST, eluted (0.5 and 1 M NaCl, respectively lanes 1 and 2 [SDC1], lanes 3 and 4 [SDC2], lanes 5 and 6 [SDC4]), then treated with heparitinase I/chondroitinase ABC (2 h) and incubated with lacritin-intein beads. Blotting is respectively with mAb B-B4 for SDC1, polyclonal antibody L-18 for SDC2 or polyclonal N-19 for SDC4 —all core protein specific. (B) Schematic diagram of human SDC1 with the dotted line indicating truncation sites in the ectodomain forming deletion constructs: 'del 1-51', 'del 51-252', and 'del 51-310'. Boxes represent PSIPRED-predicted alpha helices. Wavy lines represent HS and CS. TM, transmembrane domain. (C) Comparative incubation of FGF2-GST and lacritin-intein beads with human SDC1 or human SDC1 'del 1-51' lysates from stably expressing HEK293T cells. After incubation, beads were washed extensively, then either treated with heparitinase I/chondroitinase ABC (+) or left untreated (−). Beads were centrifuged, and pellets (P) and supernatants (S) blotted with mAb B-B4 for SDC1 core protein. Lysate from HEK293T cells stably expressing SDC1 'del 1-51' is blotted in lanes 6, 7. (D) Comparative incubation of lacritin-intein beads with human SDC1 'del 51-252', 'del 1-51' or 'del 51-310' lysates from stably or transiently expressing HEK293T cells. 'pcDNA' is lysate from cells transfected with vector only. After incubation, beads were washed extensively, then treated with heparitinase Uchondroitinase ABC. Beads were centrifuged, and pellets blotted with mAb 3G10 for desaturated uronates in SDC1.
Figure 7B:
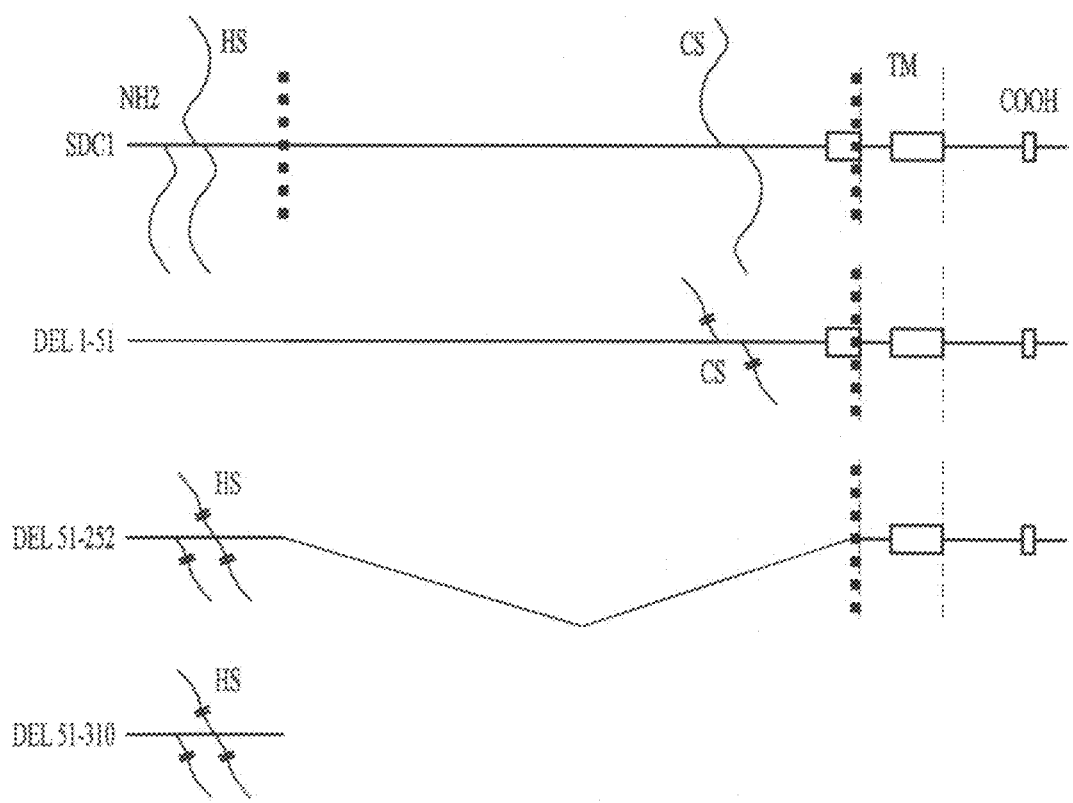
Figure 7C:
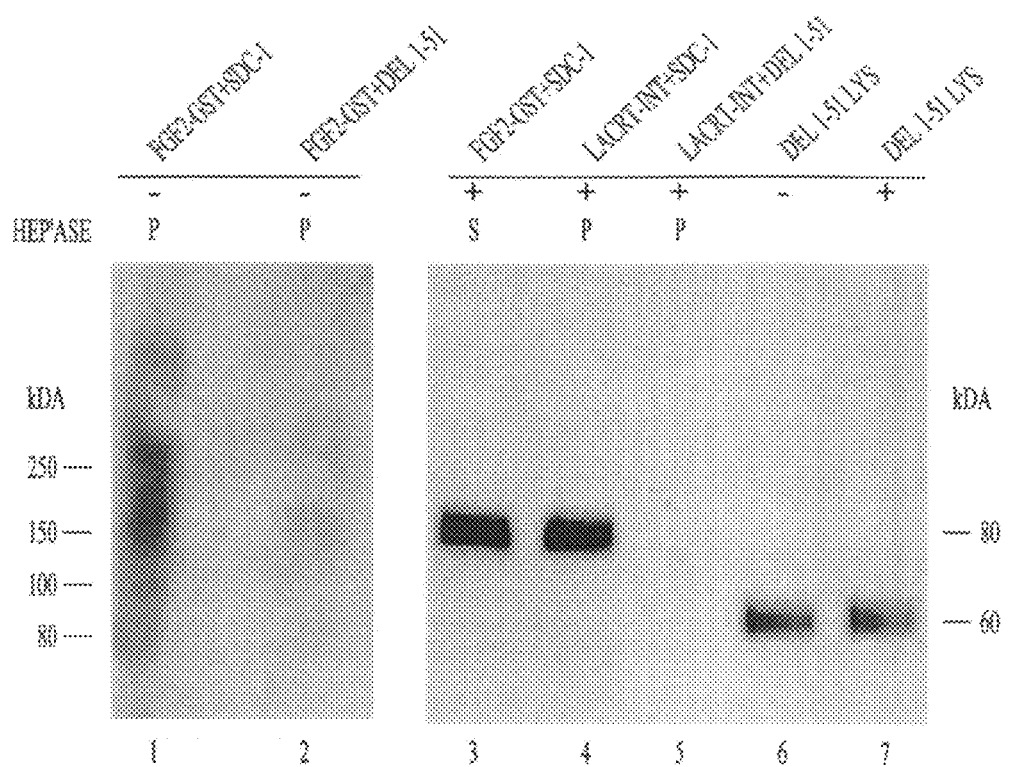
Figure 7D:
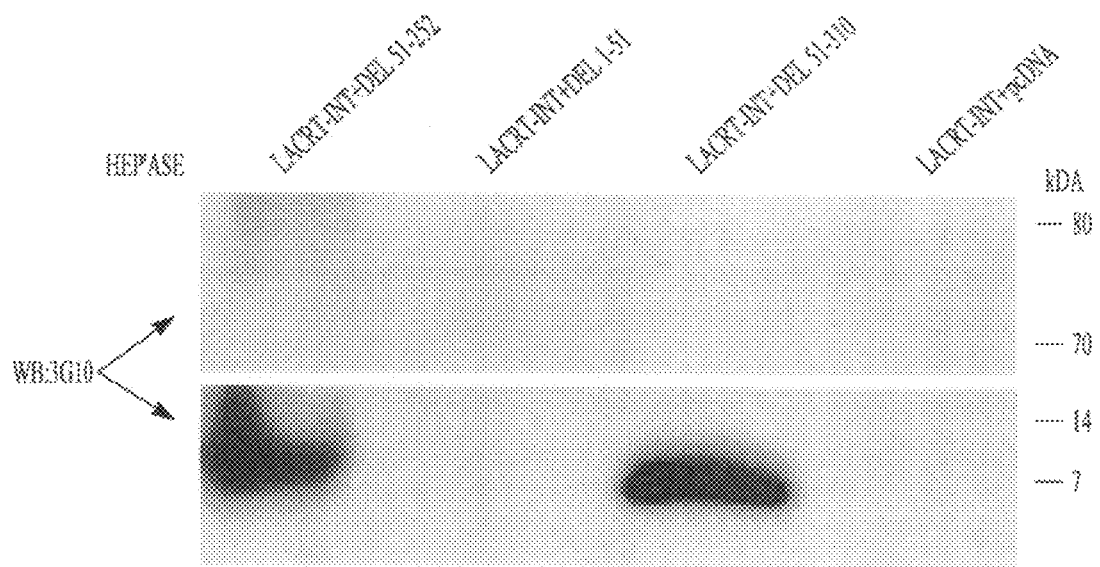

One hypothesis to explain these data is that heparanase-sensitive HS sterically blocks lacritin binding to a latent core protein site in native SDC1. If this is true, heparitinase digestion of native SDC1 should promote lacritin binding (FIG. 7A). To study this possibility, SDC1 from cell lysates was purified on FGF2-GST, washed, salt eluted, heparitinase digested, and then incubated with lacritin-intein (lane 1, 0.5 M NaCl eluate; lane 2, 1.0 M NaCl eluate). As controls, SDC2 and SDC4 from cell lysates were individually purified on FGF2-GST, washed, salt eluted, heparitinase digested, and then also incubated with lacritin-intein (SCD2: lane 3, 0.5 M NaCl eluate; lane 4, 1.0 M NaCl eluate; and SCD4: lane 5, 0.5 M NaCl eluate; lane 6, 1.0 M NaCl eluate). Affinity precipitates were heparitinase/chondroitinase (+) treated prior to SDS-PAGE and blotting for SDC1, SDC2 or SDC4. We observe that FGF2-purified SDC1, but not FGF2-purified SDC2 or SDC4, can indeed bind lacritin after heparitinase treatment (FIG. 7A, lanes 1, 2), presumably by exposing a hidden site.

Where does lacritin bind? Steric hindrance by the N-terminal HS chains suggests that lacritin may bind SDC1's N-terminus. However binding might occur elsewhere when consideration is given to HS chain length and core protein folding. To examine these possibilities, we generated cell lines stably or transiently expressing human SDC1 lacking 51 N-terminal amino acids ('del 1-51'), or lacking amino acids 51-252 of the ectodomain ('del 51-252'), or retaining only the N-terminal 50 amino acids as a secreted form (' del 51-310') (FIG. 7B). Del 51-252 and del 51-310 both bound lacritin, but not del 1-51 (FIG. 7C, D), suggesting that SDC1's N-terminus is recognized by lacritin.

Figure 8A:
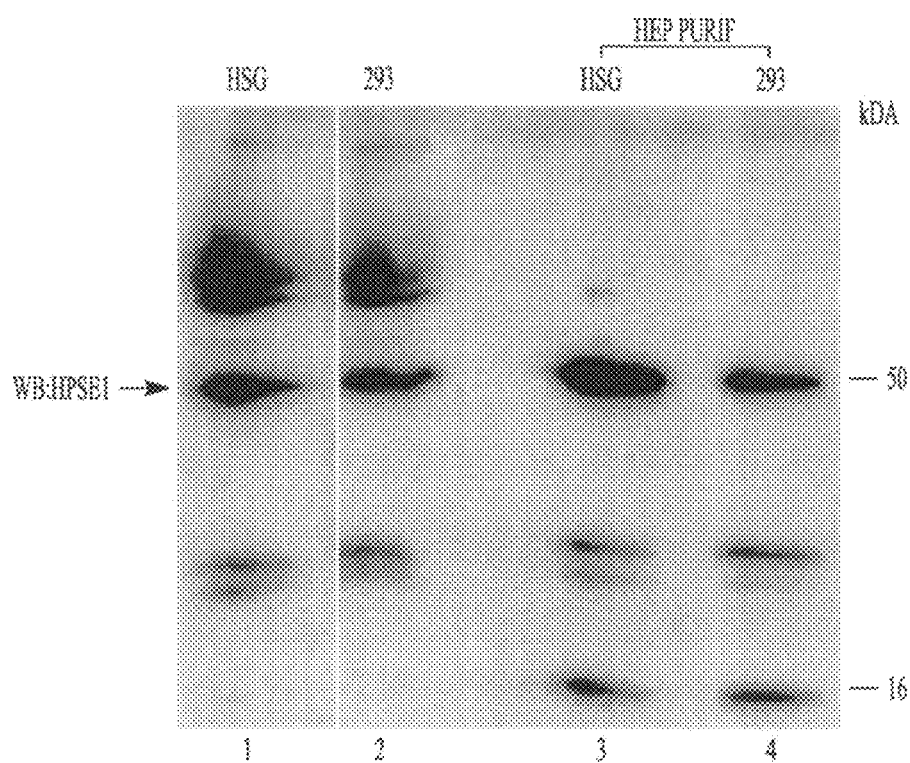
FIG. 8. Heparanase is expressed by HEK293T and HSG cells and is required for lacritin-dependent mitogenesis. (A) Lysates of HSG cells (lane 1) and HEK293T cells stably expressing human SDC1 (lanes 2), versus 2 M NaCl eluant of each after incubation with HiTrap heparin affinity columns (respectively lanes 3, 4). Blotting is with polyclonal anti-human heparanase-1 (HPSE1) antibody. (B) Lysates from HSG cells that had been mock transfected, or transfected with 1 nM heparanase-1 siRNA. Blotting is with polyclonal anti-human HPSE1 or anti-tubulin antibodies. (C) Proliferation assay in which HSG cells were treated with 10 nM lacritin or 1 nM EGF 48 h after being mock transfected, or transfected with 10 nM of Ambion's negative control siRNA #1 (neg), 1-100 nM HPSE1 siRNA, or 1 nM HPSE2 siRNA. Some HPSE1 siRNA cells were lacritin treated for 24 h in the presence of 1 µg of heparanase-enriched eluant (A, above) from HEK293T cells stably expressing SDC1 ('1 nM+HPSE') or 0.0001 U of bacterial heparitinase. (D) Sepharose CL-6B gel filtration chromatography of HS from lacritin and FGF2 affinity enriched SDC1 isolated from normal or HPSE1 depleted HSG cells. Lysates from cells labeled with 50 µCi/ml $Na_2^{35}SO_4$ in DMEM for 48 h were affinity precipitated with FGF2-GST or lacritin-intein. Equal microgram amounts of SDC1 bound to beads was digested with chondroitin ABC lyase to remove CS, eluted with 2 M NaCl and then subjected to $NaBH_4$ eliminative cleavage. Released HS was neutralized by drop wise addition of 1 M HCl and then subjected to Sepharose CL-6B gel filtration chromatography to compare relative size of HS chains. V0, void volume (dextran blue); Vt, total volume (sodium dichromate).
Figure 8B:
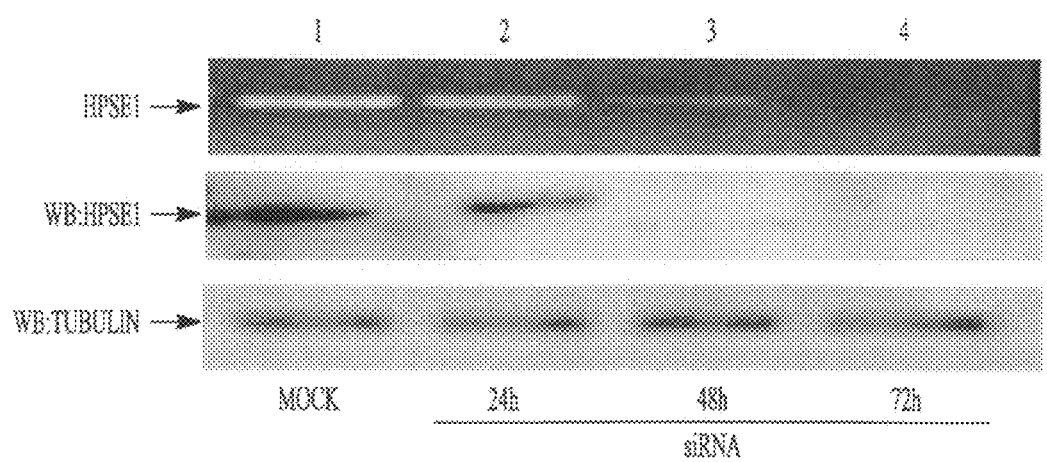
Figure 8C:
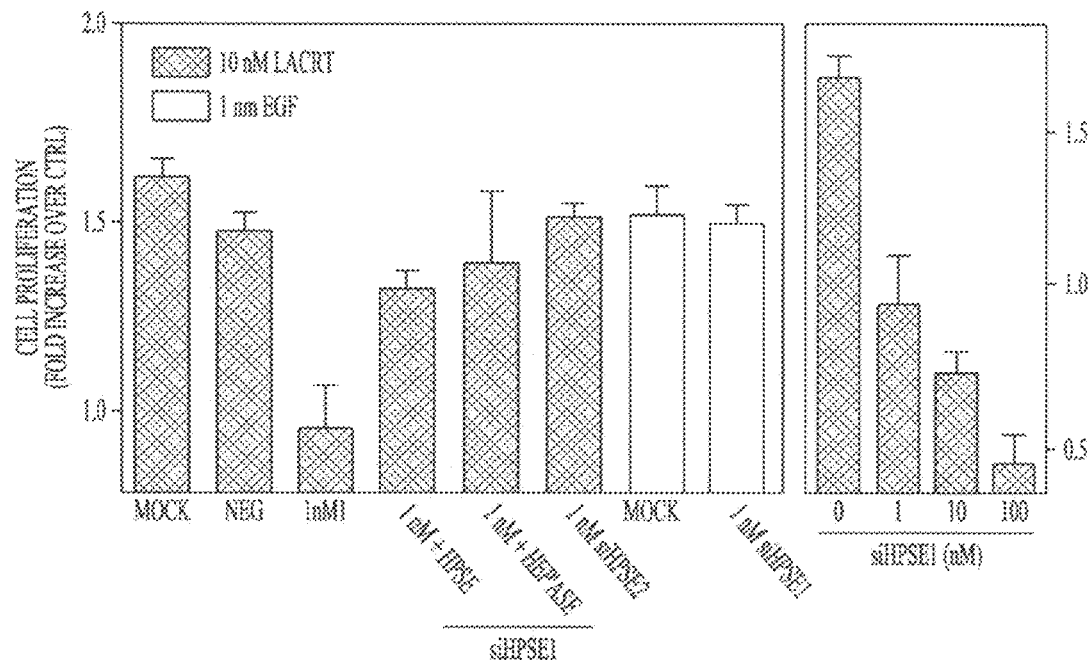

Although most heparanase is associated with endocytic compartments, the argument for an active cell surface role is compelling. Evidence includes heparanase secretion by activated endothelial (Chen et al., 2004) and T cells during inflammation (Fridman et al., 1987), antisense-inhibited cancer dissemination (Uno et al., 2001), and overexpression-associated migration of hair stem cell progeny (Zcharia et al., 2005). Is heparanase required for lacritin mitogenic binding of SDC1? Blotting for heparanase-1 detected the active 50 kDa form that was enrichable on a HiTrap heparin column from both HSG and HEK293/SDC1 lysates (FIG. 8A), in keeping with the known affinity of heparanase for heparin. The presence of heparanase in these fractions was confirmed in preliminary activity assays showing digestion of $^{35}SO_4$-labeled matrix (not shown). To assess whether heparanase-1 or -2 is required for lacritin-dependent proliferation, we treated HSG cells with siRNAs for each (FIG. 8B, C). Heparanase-1 is abundantly expressed and when knocked-down reduced lacritin-dependent proliferation to background in a dose dependent manner. Importantly, the lowest effective doses did not affect EGF-dependent mitogenesis and depleted cells were rescued by addition of exogenous heparanase or heparitinase (FIG. 8C). In depleted cells without lacritin, neither had any effect (FIG. S2), thus eliminating the possibility that rescue was instead from heparanase signaling (Gingis-Velitsky et al., 2004). Heparanase-2 siRNA also had no effect (FIG. 8C) but standard RT-PCR failed to detect heparanase-2 expression in untreated cells (not shown) in keeping with real time PCR detection of <15 mRNA copies/ng cDNA in human salivary gland (McKenzie et al., 2000). Above we noted that lacritin mitogenic signaling promotes COX-2 expression downstream of NFATC1 (Wang et al, submitted), and that siRNA depletion of SDC1, but not SDC2, abrogates lacritin-dependent COX-2 expression (FIG. 5D). If heparanase-1 is functionally linked with SDC1 in lacritin mitogenic signaling, then depletion of heparanase-1 should have a similar effect. We observe in FIG. 5D that this is indeed the case. Lacritin has no effect on COX-2 expression in cells lacking heparanase-1.

Figure 8D:
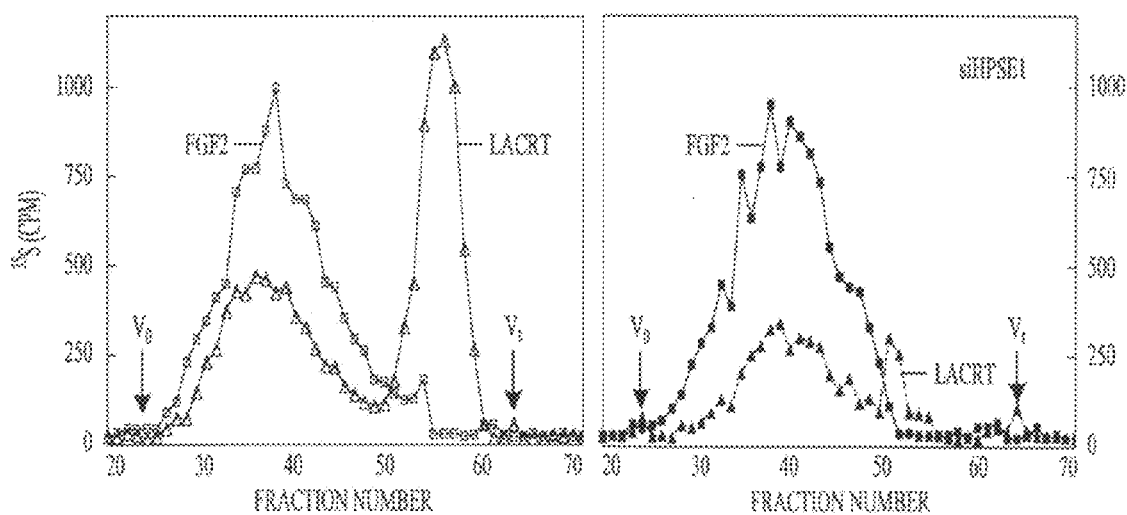
Figure 9:
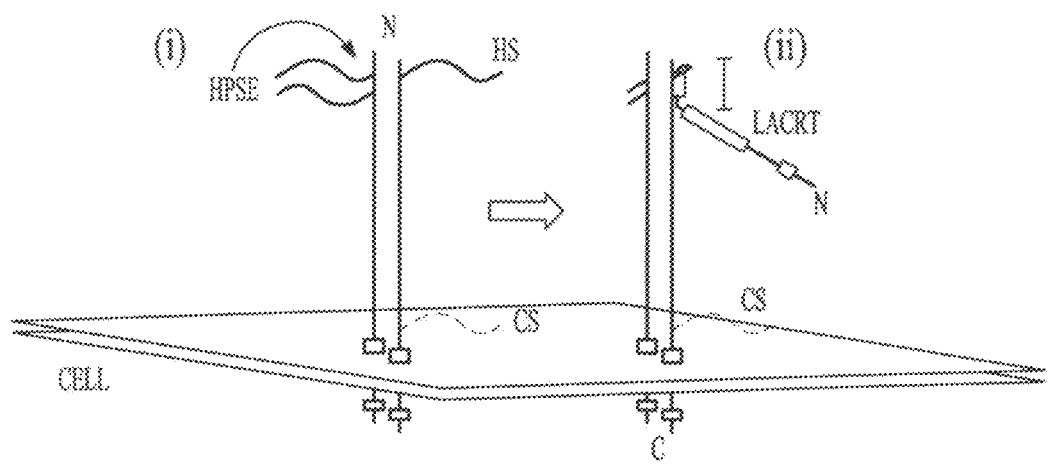
FIG. 9. Proposed model of epithelial cell targeting by lacritin. Deglycanated core protein of SDC1 targets the epithelial selective prosecretory mitogen lacritin. (i) Binding requires prior partial or complete removal of HS chains by endogenous HPSE1. (ii) Binding is mutually specified by lacritin's C-terminal mitogenic domain and SDC1's N-terminus.

Thus, it is apparent that two pools of SDC1 are available, and that the lacritin-bindable pool is likely generated by heparanase. If this is true, the distribution of HS chain sizes in the FGF2-bindable vs lacritin-bindable pools should differ. To explore this possibility, each pool was isolated by affinity precipitation from $^{35}SO_4$-labeled cell lysates. After chondroitinase digestion, and then elution with salt, HS was cleaved from the core protein with NaBH4 and analyzed by CL-6B gel filtration chromatography (FIG. 8D). In contrast to unimodal HS from the FGF2 pool (Kav=0.3-0.33; ~40 kDa), HS from the lacritin pool was bimodal with most 35SO4 eluting with a Kav of 0.75-0.8. This corresponds to approximately 4-5 kDa. Both estimates are based on Waterson's standard curve (Waterson, 1971). Interestingly, lower molecular weight HS was eliminated by heparanase-1 depletion (FIG. 8D). Taken together, these data suggest a mechanism whereby SDC1's HS-rich N-terminus is partially deglycanated by heparanase-1 to facilitate lacritin binding and signaling to mitogenic COX-2.

Discussion

How cell surface proteoglycans specify regions of epithelial morphogenesis, homeostasis or secretion is a central question in developmental biology. We report a new mechanism in which the N-terminal deglycanated core protein of SDC1 and not complete HS/CS chains nor SDC2 or SDC4, appears to target the epithelial selective prosecretory mitogen lacritin. An important and novel step in this approach is that binding necessitates prior complete or partial removal of HS chains by endogenous heparanase. Limiting lacritin activity to specific sites of secreted heparanase thus transforms widely expressed SDC1 into a regulated surface binding protein.

Recent studies emphasize a growing appreciation for an interaction role of syndecan core proteins beyond the binding accomplished by their HS chains. Sdc1 regulates the activation of the αvβ3 and αvβ5 integrins in several cell types, an interaction that depends on functional coupling between an extracellular active site in the syndecan core protein and the integrins (Beauvais and Raprager, 2003; Beauvais et al., 2004; McQuade et al, 2006). HS plus a short extracellular hydrophobic region near the transmembrane domain of mouse Sdc1 inhibits ARH-77 human B lymphoid cell invasion into collagen I (Langford et al., 2005). Recombinant human SDC2 core protein from E. coli mediates adhesion and proliferation of colon carcinoma cells (Park et al., 2002), and mouse Sdc4 contains a high affinity cell-binding domain proximal to HS attachment sites (McFall and Rapraeger, 1997, 1998). Thus, the ectodomains of syndecan core proteins mediate a number of morphogenetic and homeostatic events.

Lactitin's preference for heparanase-deglycanated SDC1 core protein is an interesting cell targeting strategy that successfully appropriates a ubiquitous proteoglycan for a role as a restrictive cell surface binding protein. That this is feasible is a reflection of the rarity of SDC1 as a part-time or hypoglycosylated proteoglycan and the lack of general ectodomain sequence conservation among syndecans. Focal heparanase release may regulate lacritin's mitogenic and prosecretory activity with unusual accuracy. Focal heparanase degradation of cell surface and extracellular matrix HS is implicated in glandular morphogenesis (Zcharia et al., 2004), stem cell migration (Zcharia et al., 2005) and cell survival (Cohen et al., 2005). It also plays a central role in inflammation and cancer (Reiland et al., 2004). Activated endothelial (Chen et al., 2004) and T cells secrete heparanase during inflammation (Fridman et al., 1987). Up-regulation of heparanase mRNA is correlated with reduced HS in invasive esophageal carcinomas (Mikami et al., 2001), whereas the opposite is linked to an increase in overall HS in differentiating myoblasts (Barbosa et al., 2005). Our studies did not address whether SDC2 and SDC4 are functional targets of heparanase. Neither bound lacritin with or without prior heparitinase treatment. Nonetheless, exploration of other ligands may reveal a similar capacity for latency in these and other HS proteoglycans.

Heparanase-regulated proliferation has previously been attributed to the release of HS-bound FGFs in metastatic breast cancer (Kato et al., 1998). Notably, the first lacritin EST in GenBank derives from a subtracted breast cancer library and evidence has been presented for lacritin gene amplification in some metastatic breast cancers (Porter et al., 2003). Others have proposed that lacritin is the second most frequent SAGE marker for circulating breast cancer cells (Bosma et al., 2002). Sdc1 is required for Wnt-dependent breast cancer in mice (Alexander et al., 2000), and in human cancers is upregulated in some but not others coincident with a role in early proliferative events (Ding et al., 2005). Thus, lacritin, heparanase, and SDC1 together potentially offer a new paradigm for some human breast cancers.

Although the sequencing data did not expose lacritin's putative signaling receptor, use of pharmacological inhibitors and siRNA have identified proximal signaling elements as Gαi or Gαo/PKCα-PLC/Ca2+/calcineurin/NFATC1/COX-2 and Gαi or Gαo/PKCα-PLC/PLD1/mTOR (Wang et al., submitted). Both are ERK1 and ERK2-independent and thus contrast with SDC1 cytoskeletal signaling. Lacritin signaling may thus involve a G-protein coupled receptor or G-protein dependent ion channel that gains ligand affinity as a consequence of lacritin immobilization on SDC1. Possibly core protein binding may be stabilized by interaction with HS stubs detected in the lower molecular weight heparanase-dependent peak (FIG. 8D). Interestingly, since lacritin- and FGF2-bindable SDC1 pools share some HS chains of similar size, not all HS on lacritin-bound SDC1 seem to be cleaved. Lack of complete competition of soluble lacritin for SDC1 in lacritin affinity precipitation assays vs N-24 might hypothetically result from folding of lacritin's more negatively charged N-terminus onto its positively charge C-terminus. Cleavage of HS by heparanase to generate lacritin-dependent mitogenic activity offers a novel mechanism of epithelial renewal with important implications to the physiology of human exocrine glands.

Taken together, these observations contribute to the growing appreciation of mechanisms by which extracellular enzymes regulate proteoglycan activity in unexpected ways. Recently described Sulf1 and Sulf2 modify the character of HS chains by selectively removing certain 6-O-sulfate groups thus altering growth factor signaling and tumor growth (Dai et al., 2005). Heparanase cleavage of HS promotes angiogenesis by solubilizing HS-bound growth factors (Sanderson et al., 2004). This new discovery that heparanase removal of HS chains removes a block to mitogenic signaling offers a new regulatory paradigm.

Example II

Figure 12A:
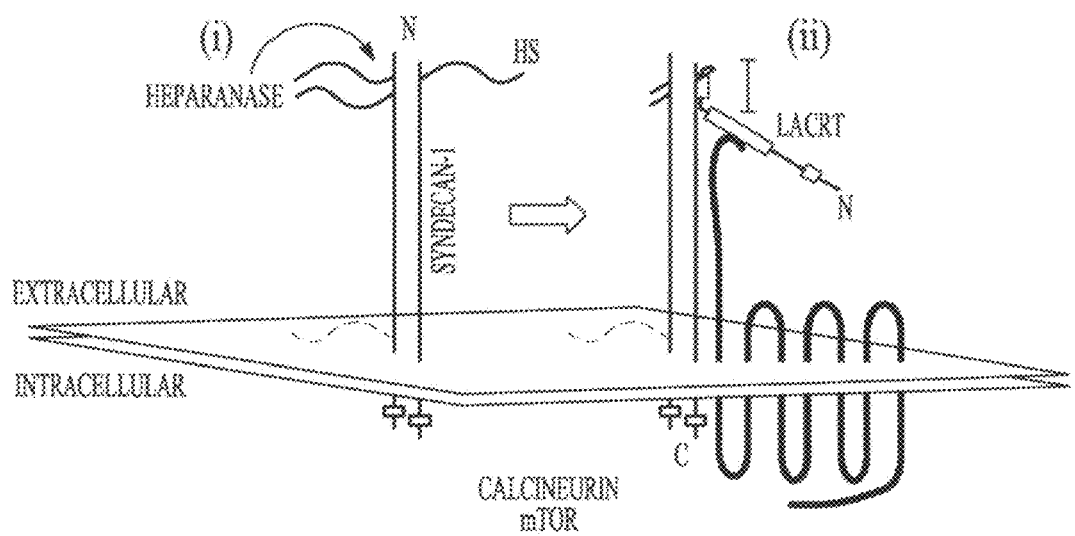
FIG. 12. A, Heparanase-dependent signaling. Removal of heparan sulfate chain(s) from syndecan-1 unblocks a lacritin binding site on an N-terminal domain of the core protein of syndecan-1 (Ma et al, '06). Syndecan-1 binding may improve lacritin's affinity for its G-protein coupled receptor (possibly ADRA2C; Ma and Laurie, unpublished), thereby activating calcineurin and mTOR signaling towards ocular surface wetting and renewal. B, Equal protein loads of human tears from normal and dry eye patients blotted for heparanase. C, Detection of heparanase released into the medium of HSG (human salivary ductal) cells after stimulation for 2 hr with 10 µM ATP, 10 µM UTP or 10 nM lacritin. HCE-T cells are also responsive (not shown).
Figure 12B:
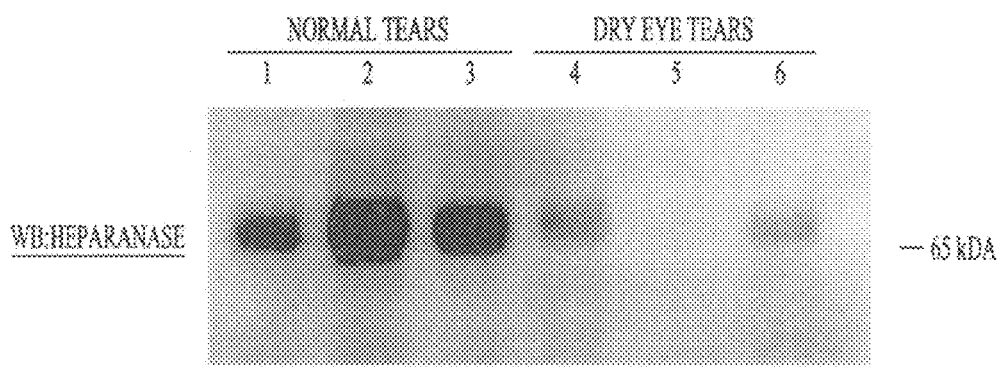
Figure 12C:
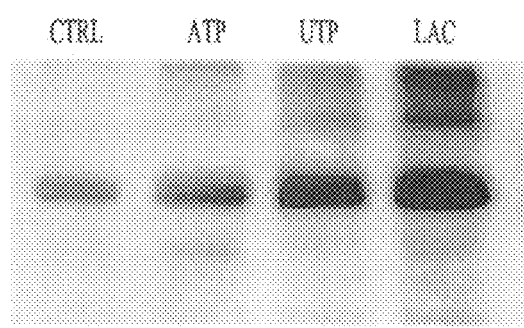

Heparanase is an 'on' switch for lacritin binding to syndecan-1 (FIG. 12A; Ma et al, '06) that in turn appears to facilitate activation of a receptor. The receptor has the signaling characteristics of a Gαi or Gαo coupled receptor (GPCR; Wang et al, '06). For heparanase to play such a central role in lacritin cell targeting, one might expect heparanase to be a normal constituent of human tears. To the best of our knowledge heparanase has not been reported in tears. Collaborator Leslie Olsakovsky (UVa Opthalmology) collected tears from normals and patients suffering from dry eye (mostly non-Sjögren's). Western blots of equal protein loads of 30 tear samples from normals vs dry eye patients suggest that heparanase is a normal tear constituent (see example blot FIG. 12B) and is substantially reduced in dry eye tears. Interestingly lacritin, UTP and ATP stimulate heparanase release (FIG. 12C). The 65 kDa form detected is the latent pro-survival form. Heparanase becomes active upon processing to 50 kDa, a form that can be detected with this antibody (Ma et al, '06). We suspect that availability of active heparanase is transient, as per the lacritin 'off/on' switch mechanism. The Inspire Pharmaceutical product INS365 for dry eye is a UTP analogue. Latent heparanase is constitutively expressed by all layers of the normal corneal epithelium in mice (Berk et al, '04). Heparanase has been implicated in glandular morphogenesis, epidermal stem cell migration and cell survival.

Figure 13:
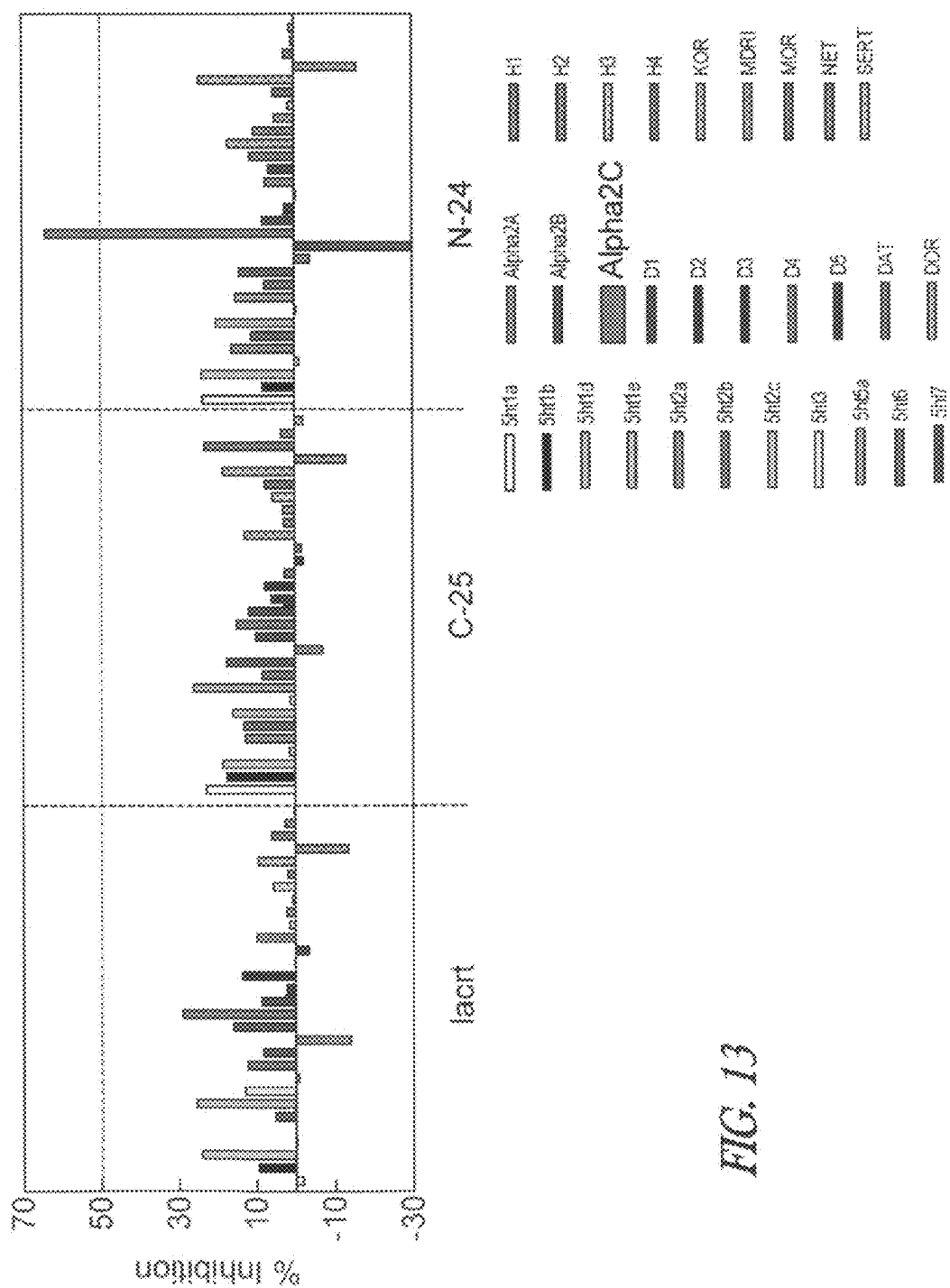
FIG. 13. Competition binding assay of lacritin, C-25 and N-24 for cloned GPCRs against radiolabeled agonist. N-24 inhibits 64% of 125I-iodoclonidine binding to the alpha-2C-adrenergic receptor ('Alpha2C' or 'ADRA2C'). Significant inhibition is considered >50% (red dashed line). Determinations were repeated four times. Assay descriptions are available to an art worker. The lacritin receptor is expected to be a GPCR because lacritin signaling is pertussis toxin sensitive (Wang et al, '06). ADRA2C couples to pertussis toxin sensitive G-proteins.

Lacritin N-24 Partially Inhibits 125I-Iodoclonidine Binding to the Alpha-2C Adrenergic Receptor. FGF2 displays low affinity binding to FGFR1 with affinity enhanced by coincident binding to syndecan-1, heparin or heparan sulfate. If we are correct that syndecan-1 increases lacritin's affinity for a G-protein coupled receptor (GPCR), possibly some low affinity GPCR binding can be detected without syndecan-1 in low salt. To ask this question, a low salt screen of 31 immobilized human GPCRs in which 10 nM lacritin, N-24 or C-25 were asked to compete with 125I-receptor ligand for receptor binding. Cutoff is 50% inhibition. N-24 lacritin (64%), but not intact lacritin (29%) or inactive C-25 (15%), competed for binding to the alpha-2C-adrenergic (ADRA2C) receptor with an equilibrium dissociation constant (Ki) of 1289±121 nM in repeated assays (FIG. 13). Although preliminary, this compares to 1698 nM for native agonist epinephrine. Possibly N-24's lack of seven negatively charged residues may improve binding in the absence of syndecan-1.

Figure 14A:
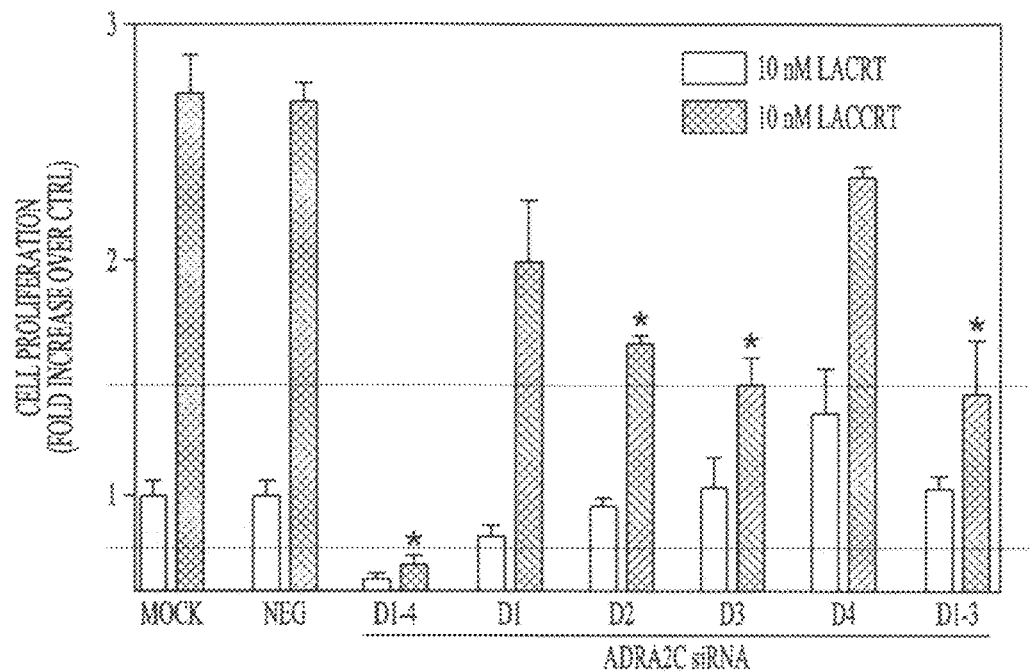
FIG. 14. LEFT, Lacritin-dependent mitogenesis by mock or lamin siRNA (negative control; 'neg') transfected cells contrasts with the full or partial inhibitory effect of transfecting with ADRA2C siRNA. D1-4 pool is most effective, followed by D1-3, D3 and D2 (asterisks). D1 and D4 have minimal effect. Cells were transfected with 10 nM pooled and individual siRNAs as described for PKC☐ in FIG. 4 of Wang et al ('06). RIGHT, RT-PCR of ADRA2C at 0, 24 and 48 hrs after siRNA transfection with 10 nM D1-4.
Figure 14B:
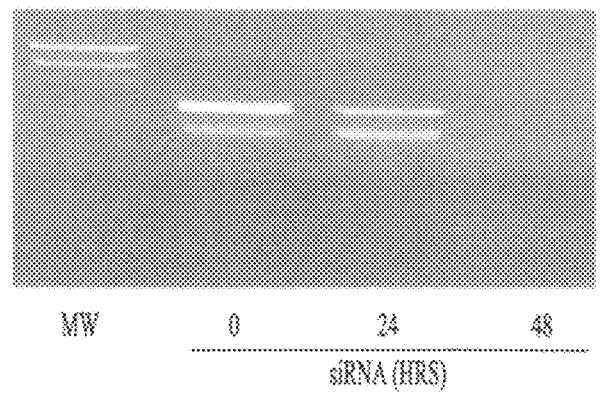
Figure 15A:
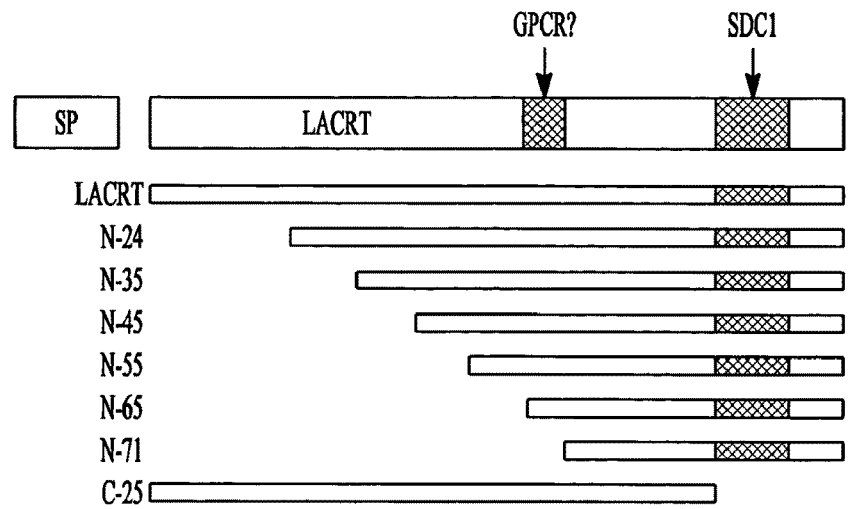
FIG. 15. LEFT, new N-terminal lacritin deletions (N-24 previously tested) with full length lacritin and negative control C-25. A signaling receptor binding site ('GPCR?') is hypothetically suggested by loss of activity with removal of six N-amino acids (KSIVEK (SEQ ID NO: 1)) from N-65. Black box indicates region of syndecan-1 (SDC1) binding. RIGHT, proliferation of subconfluent HCE-T cells treated with 10 nM of each deletion construct in serum-free medium (Wang and Laurie, unpublished). EGF serves as a positive control. Proliferation was determined by 3H-thymidine uptake (Wang et al, '06; Ma et al, '06). Absolute fold-increase values between FIGS. 14 and 15 are not comparable because lacritin preps differ.
Figure 15B:
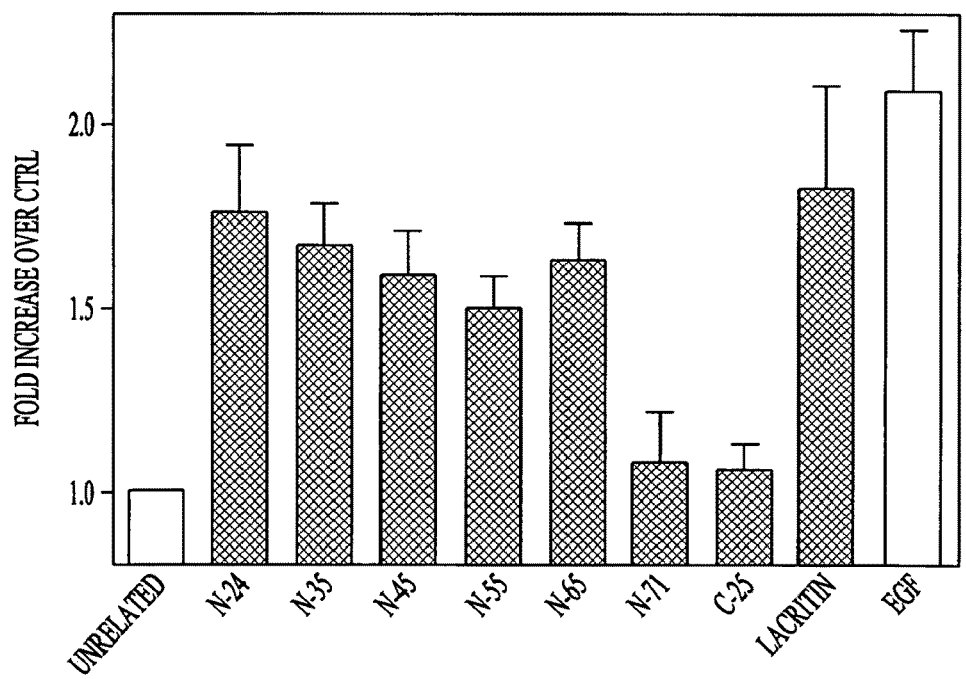
Figure 16:
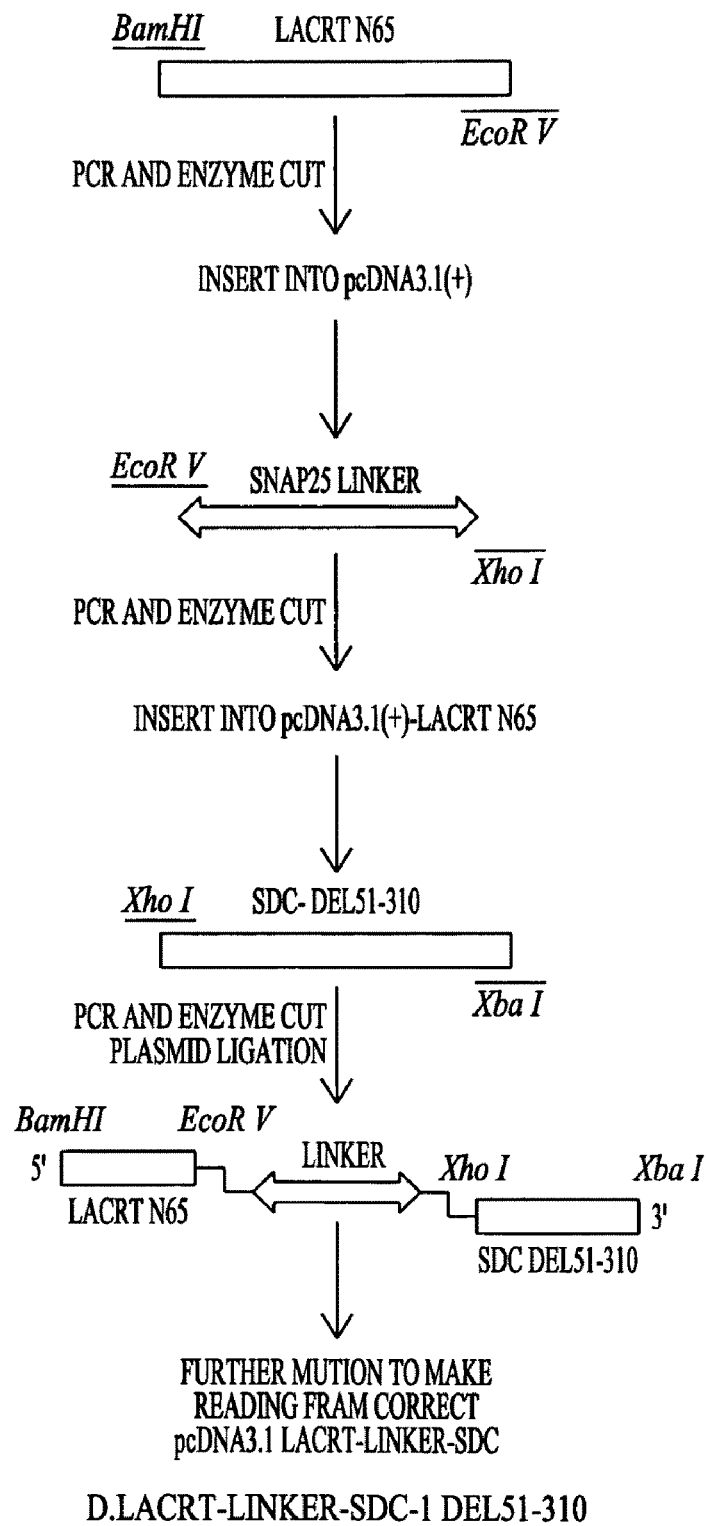
FIG. 16. An example of a preparation of a lacritin/syndecan fusion protein.

We depleted ADRA2C by transfecting with 10 nM pooled or individual siRNAs to ADRA2C (FIG. 14). Pooled siRNAs D1-D4 reduced lacritin responsiveness below baseline. We then transfected individual or D1-3 pooled siRNAs. D3 and D1-3 reduced the lacritin-dependent mitogenesis by almost 50%, whereas D1 and D4 were less effective. Individual siRNAs had no effect on FBS-stimulated mitogenesis (not shown). ADRA2C is Gαi or Gαo coupled (pertussis toxin sensitive) and expressed by normal human conjunctival (Diebold et al, '05) and corneal (Huang et al, '95) epithelia. ADRA2C is best known as a neural receptor involved in the regulation of sympathetic neurotransmitter release. Little is known of its role on epithelial cells.

Lacritin N-Terminal Deletion Analysis Suggests a Putative Signaling Receptor Binding Site. Syndecan-1 binds lacritin's C-terminus (Ma et al, '06). Where might the hypothetical signaling receptor bind? A series of lacritin N-terminal deletion mutants were developed, expressed and purified by our JMU collaborators. Subconfluent HCE-T cells in serum-free medium were treated with each in our standard 3H-thymidine mitogenesis assay. N-24, N-35, N-45, N-55, N-65 and lacritin are all mitogenic. Activity is lost when the amino acids KSIVEK (SEQ ID NO: 1) are removed from N-65. Peptide-Structure and Helical Wheel analyses implicate this region as another amphipathic α-helix. Interestingly, the lacritin alternative splice form 'lacritin-b' lacks the sequence SIVEKSILLTE (SEQ ID NO: 22) (Ma et al, '07), and alternative splice form 'lacritin-c' has a completely novel C-terminus, lacking both this site and the syndecan-1 binding site. This suggests that lacritin-b and -c would be inactive.

Discovery of Lacritins in Lower Species: Conservation of Two Binding Motifs. New public genomic sequencing (Sanger Institute Ensembl website) has recently revealed a number of novel lower species lacritins. Putative lacritin orthologues were detected in armadillo, domestic cat, lesser hedgehog, microbat, tree shrew and common shrew. We expect this list to expand as more species are sequenced to completion. We extracted each sequence then constructed a Phylogram using GrowTree (not shown). Chimp and tree shrew lacritins are respectively the most and least identical to human lacritin. We also aligned each using ClustralW+. Interesting regions of conservation include KSIVEK (SEQ ID NO: 1) and the C-terminal syndecan-1 binding site (not shown). We performed helical wheel analysis on sequences from the latter. The putative amphipathic α-helix (Wang et al, '06) appears to be conserved in all species and thus most may be capable of binding syndecan-1, as per human lacritin (Ma et al, '06).

Headings are included herein for reference and to aid in locating certain sections. These headings are not intended to limit the scope of the concepts described therein under, and these concepts may have applicability in other sections throughout the entire specification.

The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention.

BIBLIOGRAPHY

Alexander, 2000, Nat. Genet. 25: 329-332.
Barbosa, 2005, J. Cell Sci. 118: 253-264.
Barden, 1997, J. Biol. Chem. 272: 29572-29578.
Beauvais, 2003, Exp. Cell Res. 286:219-232.
Beauvais, 2004, J. Cell. Biol. 167:171-181.
Bosma, 2002, Clin. Cancer. Res. 8: 1871-1877.
Capurro, 2005, Cancer. Res. 65: 6245-6254.
Chen, 2004, Biochem. 43: 4971-4977.
Chen, 1997, Am. J. Physiol. 272: 494-503.
Cohen, 2006, Int. J Cancer 118: 1609-1617.
Couchman, 2003, Nat. Rev. Mol. Cell. Biol. 4: 926-937.
Da, 2005, J. Biol Chem. 280:40066-40073.
David, 1992, J. Cell Biol. 119:961-975.
Deepa, (2004), J. Biol. Chem. 279:37368-37376.
Ding, 2005, J. Cell Biol. 171:729-738.
Dor, 2004, Nature. 429: 41-46.
Esko, 200, Ann. Rev. Biochem. 71: 435-471.
Fridman, 1987, J. Cell Physiol. 130:85-92.
Gingis-Velitski, 2004, J. Biol. Chem. 279:23536-23541.
Häcker, 2005, Nat. Rev. Mol. Cell. Biol. 6: 530-541.
Kato, 1998, Nat. Med. 4: 691-697.
Langford, 2005, J. Biol. Chem. 280: 3467-3473.
McFall, 1997, J. Biol. Chem. 272: 12901-12904.
McFall, 1998, J. Biol. Chem. 273: 28270-28276.
McKenzie, 2000, Biochem. Biophys. Res. Commun. 276: 1170-1177.
McQuade, (2006), J. Cell Sci., in press.
Mikami, 2001, Jpn. J. Cancer Res. 92:1062-73.
Park, 2002, J. Biol. Chem. 277: 29730-29736.
Perrimon, 2000, Nature 404:725-728.
Porter, 2003, Proc. Natl. Acad. Sci. USA. 100:10931-10936.
Radtke, F, and H. Clevers. 2005. Science. 307: 1904-1909.
Reiland, 2004. J. Biol. Chem. 279:8047-8055.
Sanderson, 2004. Matrix Biol. 23:341-352.
Sanghi, 2001. J. Mol. Biol. 310: 127-139.
Siemeister J. Biol. Chem. 273: 11115-11120.
Uno 2001. Cancer Res. 61: 7855-7860.
Utani 2001. J. Biol Chem. 276:28779-28788.
Viviano 2004 J. Biol. Chem. 279:5604-5611.
Wang 2004, Dev. Biol. 273:1-22.
Wang, 2006, J Cell Biol, online publication, Aug. 21, 2006, 10.1083/jcb.200605140.
Wasteson, A. 1971, J Chromatogr. 59:87-97.
Zako, J. Biol. Chem. 278: 13561-13569.
Zcharia, 2004, FASEB J. 18: 252-263.
Zcharia, 2005, Am. J. Pathol. 166: 999-1008.

What is claimed is:

1. A fusion protein comprising lacritin (SEQ ID NO:4) and the N-terminus portion of syndecan-1 (SEQ ID NO:12), wherein the N-terminus portion of syndecan-1 comprises amino acids 1-51.

2. A composition comprising the fusion protein of claim 1.

3. A method to induce proliferation in epithelial cells responsive to a lacritin polypeptide, said method comprising contacting said cells with a composition comprising an effective amount of the fusion protein of claim 1.

* * * * *